US009524552B2

(12) United States Patent
Wang et al.

(10) Patent No.: US 9,524,552 B2
(45) Date of Patent: Dec. 20, 2016

(54) 2D/3D REGISTRATION OF A DIGITAL MOUSE ATLAS WITH X-RAY PROJECTION IMAGES AND OPTICAL CAMERA PHOTOS

(75) Inventors: Hongkai Wang, Los Angeles, CA (US); Arion F. Hadjioannou, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 442 days.

(21) Appl. No.: 13/564,675

(22) Filed: Aug. 1, 2012

(65) Prior Publication Data
US 2013/0034203 A1    Feb. 7, 2013

Related U.S. Application Data

(60) Provisional application No. 61/574,514, filed on Aug. 3, 2011.

(51) Int. Cl.
*A61B 6/00* (2006.01)
*G06T 7/00* (2006.01)
*A61B 6/03* (2006.01)

(52) U.S. Cl.
CPC .............. *G06T 7/0032* (2013.01); *A61B 6/03* (2013.01); *A61B 6/508* (2013.01); *A61B 6/5247* (2013.01); *A61B 6/583* (2013.01); *A61B 2503/40* (2013.01); *G06K 2209/051* (2013.01);
(Continued)

(58) Field of Classification Search
USPC .......................................................... 378/63
See application file for complete search history.

(56) References Cited

U.S. PATENT DOCUMENTS 6,583,420 B1 * 6/2003 Nelson ................. A61B 6/4233
  250/363.05
7,570,738 B2 * 8/2009 Khamene ............... A61B 6/032
  378/20

(Continued)

FOREIGN PATENT DOCUMENTS

WO    WO96/07144    3/1996

OTHER PUBLICATIONS

International Search Report and Written Opinion of PCT/US2012/049389 issued Mar. 4, 2013.

*Primary Examiner* — Phillip A Johnston
(74) *Attorney, Agent, or Firm* — Norton Rose Fulbright US LLP

(57) ABSTRACT

A method for preparing an image simulating the anatomy of a small subject test animal, and an apparatus for producing said image and an anatomical atlas for co-registering therewith, comprising the generation of two or more non-tomographic images of the test animals is described. Examples of the non-tomographic imaging modalities and the images generated include, but are not limited to one or more x-ray sources and resultant of x-ray projections, photographic cameras and resulting digital or optical images and surface scanners and resultant surface scans. The subject animal is positioned at a focal point in a carrier in an imaging enclosure. A combination of one or more of the non-tomographic images taken from different angles within the enclosure are combined and through an iterative process co-registered with the previously generated digital atlas of the anatomy of the same or similar test animals.

16 Claims, 27 Drawing Sheets

(52) U.S. Cl.
CPC ............... *G06T 2207/10072* (2013.01); *G06T 2207/10116* (2013.01); *G06T 2207/30004* (2013.01)

(56) References Cited

U.S. PATENT DOCUMENTS

| | | | |
|---|---|---|---|
| 7,734,325 B2* | 6/2010 | Vizard | A61B 5/0059 250/336.1 |
| 8,503,745 B2* | 8/2013 | Simon | A61B 6/12 382/128 |
| 8,774,481 B2* | 7/2014 | Schreibmann | G06T 7/0024 378/4 |
| 2005/0018885 A1* | 1/2005 | Chen | G06T 17/00 382/128 |
| 2008/0240527 A1 | 10/2008 | Keller | |
| 2009/0175562 A1 | 7/2009 | Pan et al. | |
| 2009/0252682 A1 | 10/2009 | Hillman | |
| 2010/0119127 A1 | 5/2010 | Bello et al. | |
| 2011/0275933 A1* | 11/2011 | Dey | A61B 6/037 600/428 |

* cited by examiner

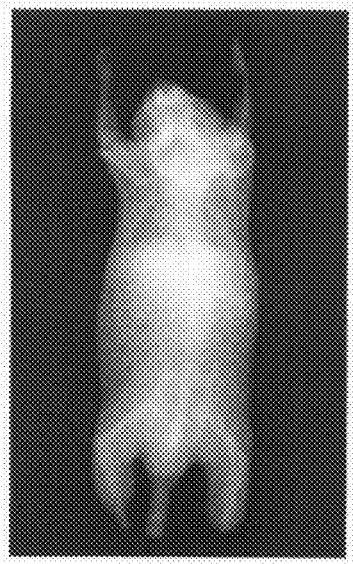
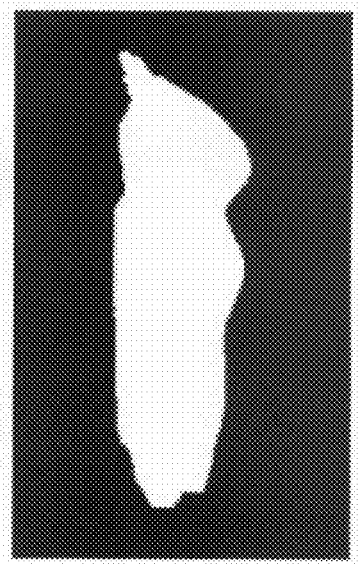
FIG. 1A  FIG. 1B
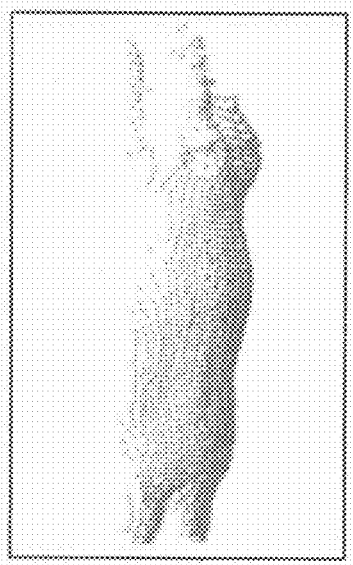
FIG. 1C  FIG. 1D

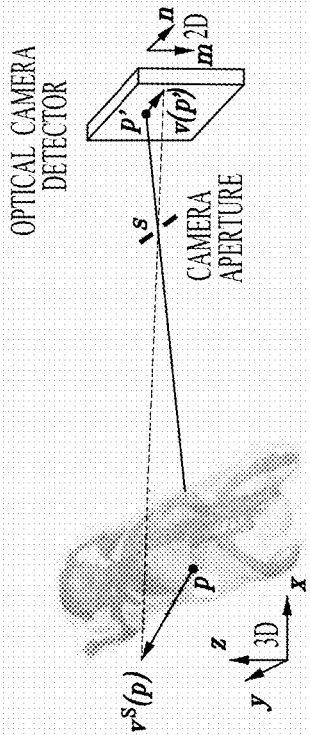
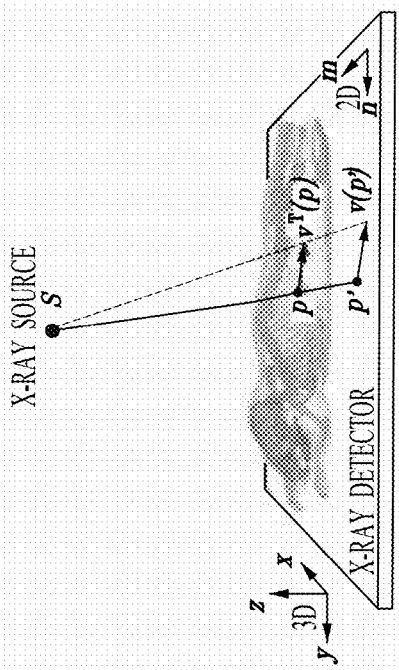
FIG. 4B
FIG. 4A

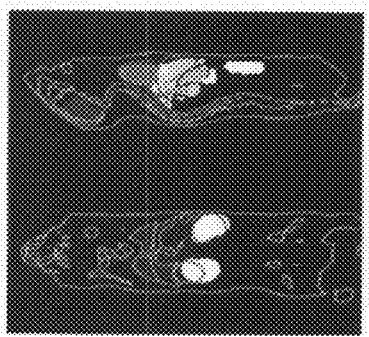
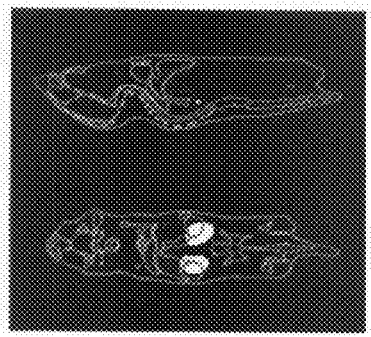
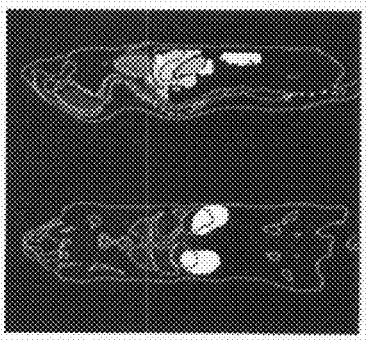
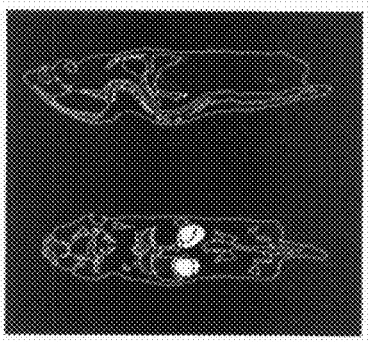
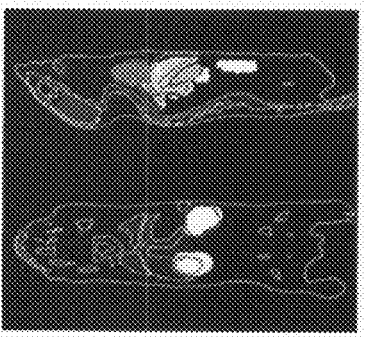
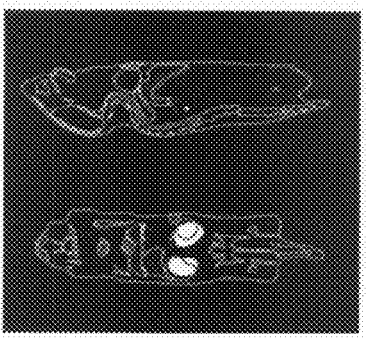
FIG. 5

2D/3D REGISTRATION OF A DIGITAL MOUSE ATLAS WITH X-RAY PROJECTION IMAGES AND OPTICAL CAMERA PHOTOS

This application claims benefit of U.S. Provisional Application 61/574,514 filed Aug. 3, 2011.

This invention was made with Government support under Grant No. CA092865, awarded by the National Institutes of Health. The Government has certain rights in this invention.

BACKGROUND

The laboratory mouse is widely used as animal model in pre-clinical cancer research and drug development. Acquiring actual anatomy of a laboratory animal, such as a mouse, is frequently needed for localizing and quantifying functional changes. Currently in vivo imaging of mouse anatomy is achieved with PET, SPECT, and optical imaging modalities or tomographic imaging systems such as micro-CT and micro-MR as imaged with modalities. Also, anatomical imaging is used to measure organ morphometry, quantify phenotypical changes and build anatomical models. In pre-clinical small animal studies, in vivo estimation of the mouse anatomy is also important to aid in localizing functional changes and measuring organ morphometry. Some molecular imaging modalities also need complimentary anatomical information to help with image acquisition, reconstruction and analysis, such as micro-SPECT scan-planning optical tomography reconstruction, micro-PET attenuation correction and tissue uptake quantification.

Currently, anatomical context is provided with tomographic x-ray CT systems that are either directly attached to the functional imaging system, or have a co-registered field of view and use specialized imaging chambers. In vivo imaging of the mouse anatomy using small animal tomographic imaging systems, such as micro computed tomography (micro-CT) and micro magnetic resonance imaging (micro-MR) systems can provide 3D tomographic images with micron-level resolution (≤100 μm for in vivo imaging of both modalities). Multiple approaches have been developed to delineate organ regions from micro-CT and micro-MR images based on image segmentation or atlas registration. However, these systems present expensive infrastructure, operation and maintenance costs which greatly diminish their dissemination potential.

An important limitation of current in vivo micro-CT technology is the low soft tissue contrast. Due to a tradeoff between acquisition time, radiation dose and image quality, standard imaging protocols of in vivo micro-CT scans normally use low-dose X-rays and a limited number of projections, resulting in low soft tissue contrast. Although contrast agents for soft tissues can be applied, the use of contrast agents increases study cost and complexity. Therefore, most pre-clinical studies still use non-contrast enhanced micro-CT images, and segmentation of soft organs from non-contrast micro-CT images remains problematic. It is therefore desirable to develop an approach to enable the estimation of 3 dimensional internal mouse anatomy from low-cost non-tomographic imaging systems.

Several mouse atlas registration approaches have been proposed for micro-CT images (Baiker M, Milles J, Dijkstra J, Henning T D, Weber A W, Que I, Kaijzel E L, Lowik C W, Reiber J H, Lelieveldt B P. Atlas-based whole-body segmentation of mice from low-contrast micro-ct data. Med Image Anal; 14(6): 723-37) and micro-MR images (Kovacevic N, Hamarneh G, Henkelman M. Medical image computing and computer-assisted intervention-miccai 2003, pp. 870-877, 2003). Other methods address mouse atlas registration with low-cost hardware such as surface laser-scanners (Joshi A A, Chaudhari A J, Li C, Dutta J, Cherry S R, Shattuck D W, Toga A W, Leahy R M. Digiwarp: A method for deformable mouse atlas warping to surface topographic data. Phys Med Biol; 55(20): 6197-214) and optical cameras (Baiker M, Vastenhouw B, Branderhorst W, Reiber J H C, Beekman F, Lelieveldt B P F. Atlas-driven scan planning for high-resolution micro-spect data acquisition based on multi-view photographs: A pilot study. Proceedings of Medical Imaging 2009: Visualization, Image-Guided Procedures, and Modeling, Lake Buena Vista, Fla., USA, 2009. SPIE.; Wildeman M H, Baiker M, Reiber J H C, Lowik C W G M, Reinders M J T, Lelieveldt B P F. 2d/3d registration of micro-ct data to multi-view photographs based on a 3d distance map. Proceedings of Biomedical Imaging: From Nano to Macro, 2009. ISBI '09. IEEE International Symposium on, 2009). However, these methods are either computationally expensive or semi-automatic, therefore not suitable for high-throughput applications. Further, use of micro-CT and micro-MR technologies in combination with these systems is also complicated. To avoid these problems, some researchers have turned to the use of low-cost non-tomographic imaging systems, such as optical cameras, 3D surface scanners and bench-top planar X-ray systems. Optical cameras can be used to obtain 2D body profiles which can be useful in inter-modality co-registration, respiratory motion monitoring, and 3D surface geometry reconstruction. Recent developments in 3D surface scanning techniques make it possible to build a surface scanner with consumer-market electronic devices (e.g. laser pointer, digital camera and/or pocket projector). As a result, several research prototypes and commercial products have been developed, such as the laser scanner with conical mirror and the structured light-based surface scanner. Bench-top planar X-ray systems are more expensive than optical cameras and surface scanners, but are still far less costly than fully 3D tomographic systems. With a planar X-ray projection, the anatomy of some internal structures (e.g. bones and lungs) can be readily observed. Several commercial small animal optical imaging systems have integrated planar X-ray systems as anatomical references, such as the KODAK In-Vivo Multispectral System FX and the Caliper LifeSciences IVIS® lumina XR system.

Besides laser scanners and optical cameras, a bench-top projection X-ray system can be another low-cost choice. However, no methods have used bench-top X-ray systems for mouse atlas registration. To address these requirements we have developed a fully-automatic atlas registration method dedicated to a low-cost hardware design. Preferably, the desired method combines different low-cost imaging modalities such as bench-top X-rays and optical cameras to give better estimations of the 3 dimensional organ anatomy.

Several software approaches have also been developed to register a digital mouse atlas with the non-tomographic modalities, in order to approximate 3D organ anatomy. Baiker et al. registered the mouse atlas to optical profiles of the mouse body to assist scan-planning of region-focused micro-SPECT (Baiker M, Vastenhouw B, Branderhorst W, et al. (2009) Atlas-driven scan planning for high-resolution micro-SPECT data acquisition based on multi-view photographs: a pilot study. Proc SPIE Medical Imaging; Visualization, Image-Guided Procedures, and Modeling (Lake Buena Vista, Fla., USA) 72611L-72618). Khmelinskii performed mouse atlas registrations under the guidance of multi-view optical photos (Khmelinskii A, Baiker M, Kaijzel E L, et al. (2010) Articulated whole-body atlases for small animal image analysis: construction and applications. Mol. Imag. Biol.). Zhang et al. aligned the mouse atlas with body surface reconstructed from multiple-view photos, aiming to assist fluorescence tomographic reconstruction (Zhang X, Badea C T and Johnson G A (2009) Three-dimensional reconstruction in free-space whole-body fluorescence tomography of mice using optically reconstructed surface and atlas anatomy. J Biomed Opt 14: 064010). Joshi et al. developed a Finite-Element-Model-based atlas warping method to register the atlas with laser scans of the mouse surface (Joshi A A, Chaudhari A J, Li C, et al. (2010) DigiWarp: a method for deformable mouse atlas warping to surface topographic data. Phys. Med. Biol. 55: 6197-6214). Chaudhari et al. proposed a method for registering a mouse atlas to a surface mesh acquired by a structured light scanner (Chaudhari A J, Joshi A A, Darvas F and Leahy R M (2007) A method for atlas-based volumetric registration with surface constraints for Optical Bioluminescence Tomography in small animal imaging. Proc SPIE Medical Imaging 2007: Physics of Medical Imaging 6510: 651024-651010). However, based on a review of the literature, current methods mainly focus on registration with optical modalities like optical photos and surface scans, and no method has been reported for mouse atlas registration with X-ray projections.

SUMMARY

Described herein is a new method for the estimation (simulation) of small animal anatomy from non-tomographic modalities, such as x-ray projections, optical cameras and surface scanners to provide anatomical images for in-vivo preclinical imaging systems. The process uses combinations of a x-ray projections with a photographs, to co-register the subject with a digital atlas. The resultant anatomical estimation (simulation) greatly reduces the cost and complexity of providing detailed and co-registered anatomical data for functional and metabolic imaging modalities such as PET and SPECT. The same technology can also be used to provide anatomical context for optical imaging modalities such as bioluminescence and fluorescence.

This method provides an approximation (simulation) of the 3D anatomy of a subject animal using low-cost non-tomographic systems, with an emphasis on organ level region identification. The method is demonstrated using a mouse as a subject animal. However, one skilled in the art will recognize that the techniques described herein are applicable to other animals. A prerequisite for this work is the existence of a digital mouse atlas. This atlas, in a preferred embodiment, is registered to a top-view X-ray projection, a side-view optical camera photo and/or a laser surface scan of the subject animal and helps to approximate the subject organ regions.

The method for registering a digital mouse atlas to X-ray projections and optical photos of the mouse utilizes limited projection information from a bench-top X-ray system and optical cameras to guide the atlas registration. Thus its hardware requirements are much lower than fully 3D tomographic systems. This method also allows the flexible combination of X-ray projections and optical photos from different view angles and therefore provides more freedom for hardware design. Describe herein is an atlas registration method based on the use of X-ray projection images and optical photos available from a projection X-ray system and a standard optical camera.

An atlas-based approach was evaluated for estimating the major organs in mouse micro-CT images. A statistical atlas of major trunk organs was constructed based on micro-CT images of 45 mouses. The statistical shape model technique was used to include inter-subject anatomical variations. The shape correlations between different organs were described using a conditional Gaussian model. For registration, first the high-contrast organs in micro-CT images were registered by fitting the statistical shape model, while the low-contrast organs were subsequently estimated from the high-contrast organs using the conditional Gaussian model. The registration accuracy was validated based on 23 non-contrast-enhanced and 45 contrast-enhanced micro-CT images. Three different accuracy metrics (Dice coefficient, organ volume recovery coefficient and surface distance) were used for evaluation. The Dice coefficients vary from 0.45±0.18 for the spleen to 0.90±0.02 for the lungs, the volume recovery coefficients vary from 0.96±0.10 for the liver to 1.30±0.75 for the spleen, the surface distances vary from 0.18±0.01 mm for the lungs to 0.72±0.42 mm for the spleen. The registration accuracy of the statistical atlas were compared with two publicly available single-subject mouse atlases, i.e. the MOBY phantom and the DIGIMOUSE atlas, and the results showed that the statistical atlas of 45 mice described above is more accurate than the two examples of single atlases. To evaluate the influence of the subject size, different numbers of subjects were used for atlas construction and registration. The results showed an improvement of the registration accuracy when more subjects were used for the atlas construction. The statistical atlas-based registration was also compared with the thin-plate spline based deformable registration, commonly used in mouse atlas registration. The results revealed that the statistical atlas also has the advantage of improving the estimation of low-contrast organs.

BRIEF DESCRIPTION OF DRAWINGS

FIG. 1 A shows a simulated top-view X-ray projection of the target subject; FIG. 1B Shows a simulated side-view silhouette photo of the target subject; FIG. 1C. Shows laser range data of the target subject and FIG. 1D shows registration results based on the images of (a) (b) and (c).

FIG. 4A shows a back-projecting top-view 2D deformation as a 3D image (ie., an X-ray projection; and FIG. 4B shows a back-projecting side-view 2D deformation as a 3D image (ie., a camera projection).

FIG. 5 is a composite image showing 2D/3D atlas registration results based on simulated test images using the three combinations on two test subjects.

FIG. 7A shows the simulation mechanism and result for the optical camera, FIG. 7B shows the simulation mechanism and result for the planar X-ray projection, FIG. 7C shows the simulation mechanism and result for the laser surface scanner and FIG. 7D shows an example of the combination of the three modalities.

FIG. 10A shows data for the whole body, brain and bone; FIG. 10B shows data for lungs, heart and liver; FIG. 10C shows data for the right and left kidney and FIG. 10D shows data for spleen and bladder.

FIG. 13A shows the first three eigenmodes of the shape variations of $SSM^H$ with each column showing the variation of one eigenmode, varying between $3\sqrt{\lambda_i^H}$ (top) and $-3\sqrt{\lambda_i^H}$ (bottom), FIG. 13B shows the first three eigenmodes of the shape variations of $SSM^L$, displayed in the same manner as FIG. 13A

When a Conditional Gaussian model is applied, represented by (h), probability maps of the registered organs are overlaid, as shown in (i) with the target CT image shown in (j).

Figure 15:
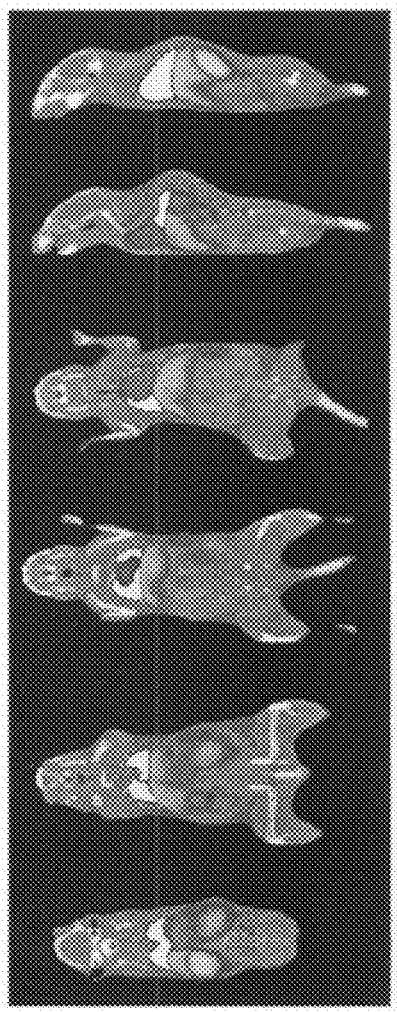

FIG. 15 shows. registration results of organ probability maps overlaid on non-contrast micro-CT images of different subjects demonstrating different coronal and sagittal slices.

Figure 16:
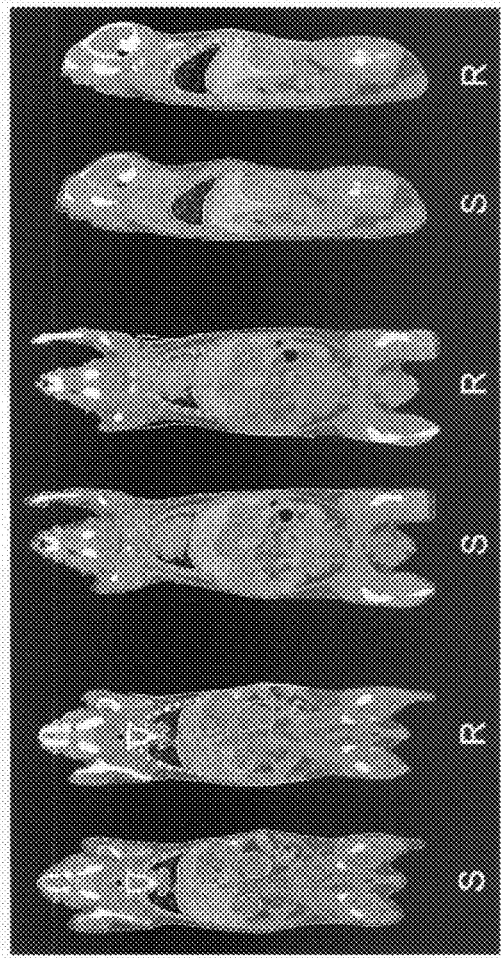

FIG. 16 shows a visual comparison of the registration results with manual segmentation results, based on contrast-enhanced micro-CT images.

Figure 17A:
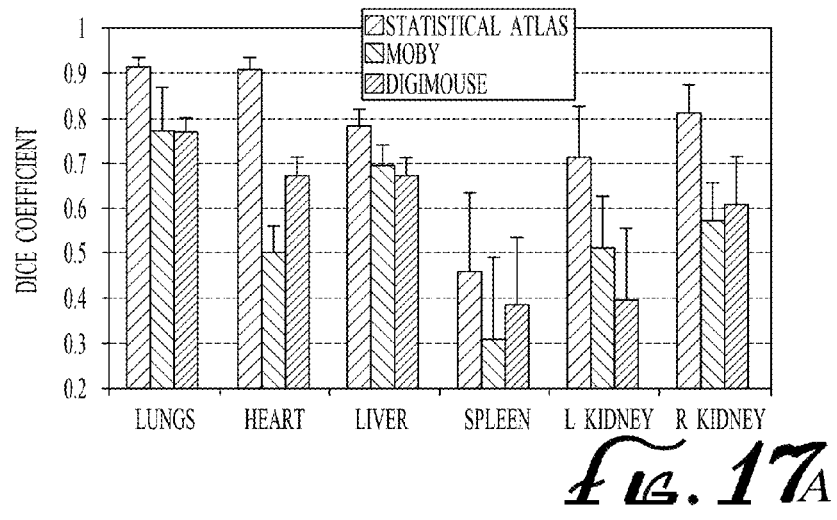
Figure 17B:
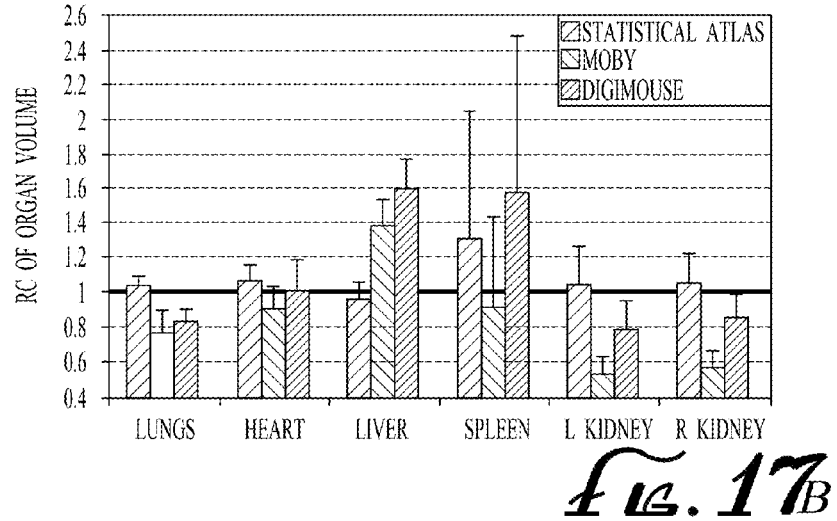
Figure 17C:
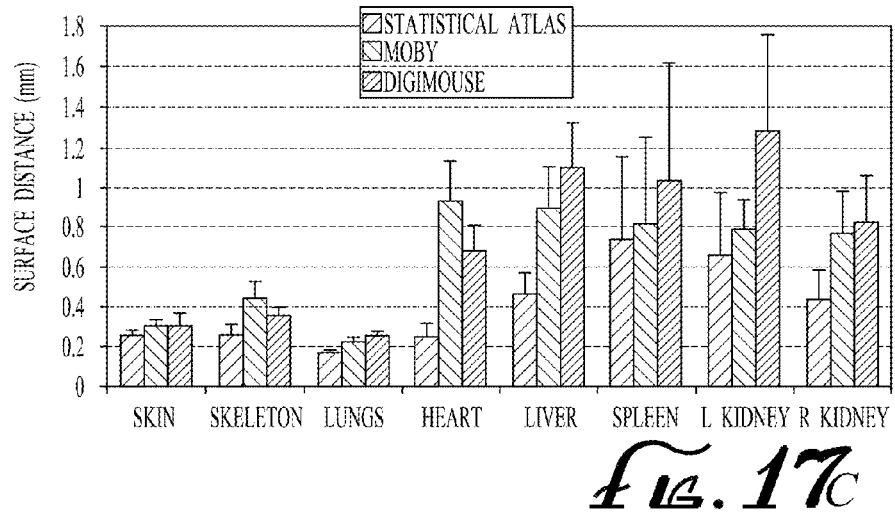

FIGS. 17A, 17B and 17C are graphs showing a comparison of registration accuracies between statistical atlas-based registration and FIG. 17B single atlas-based registrations with FIG. 17A comparing results of Dice coefficient., (b) comparing results of recovery coefficients of organ volume and FIG. 17C comparing results of surface distance.

Figure 18:
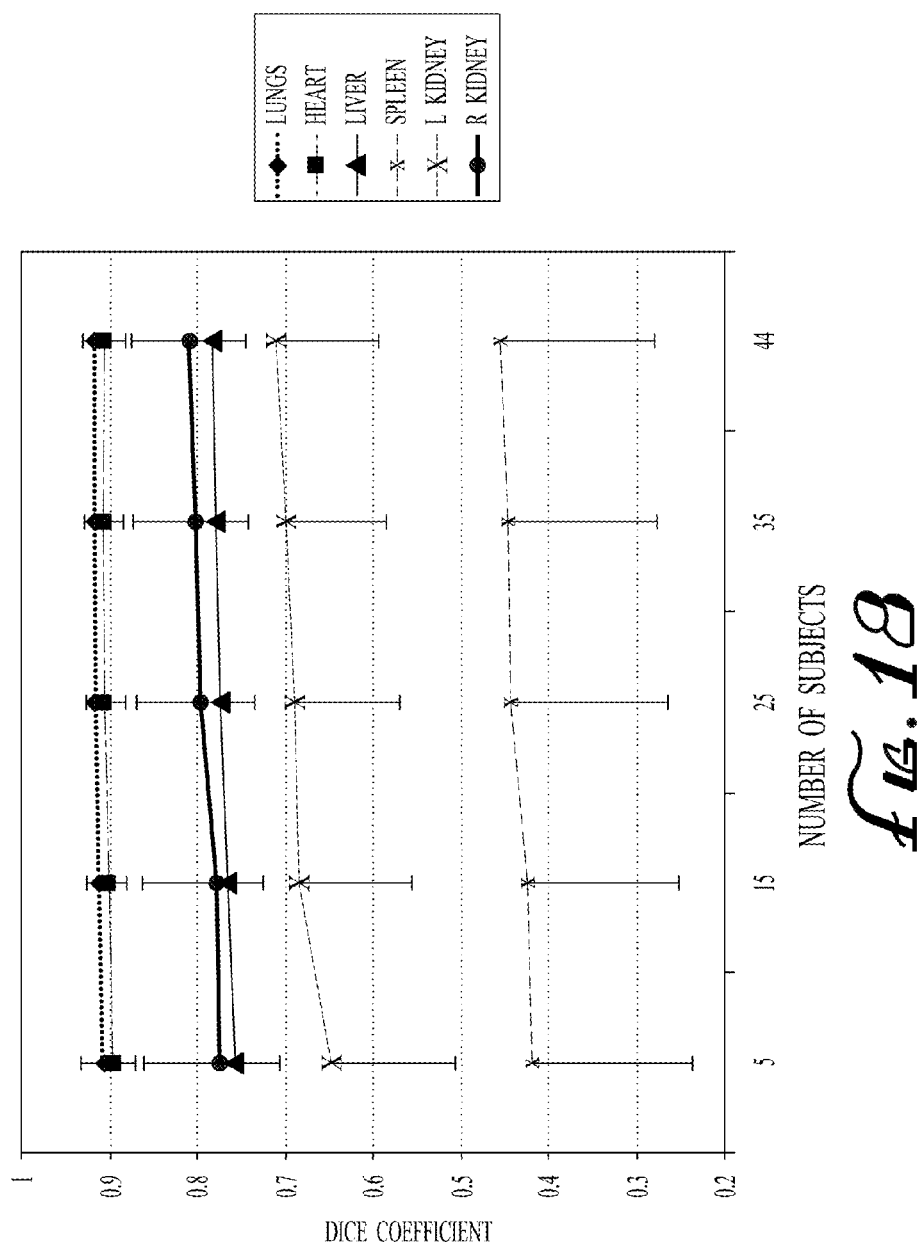

FIG. 18 is a graph showing the influence of the number of subjects on registration accuracy.

Figure 19:
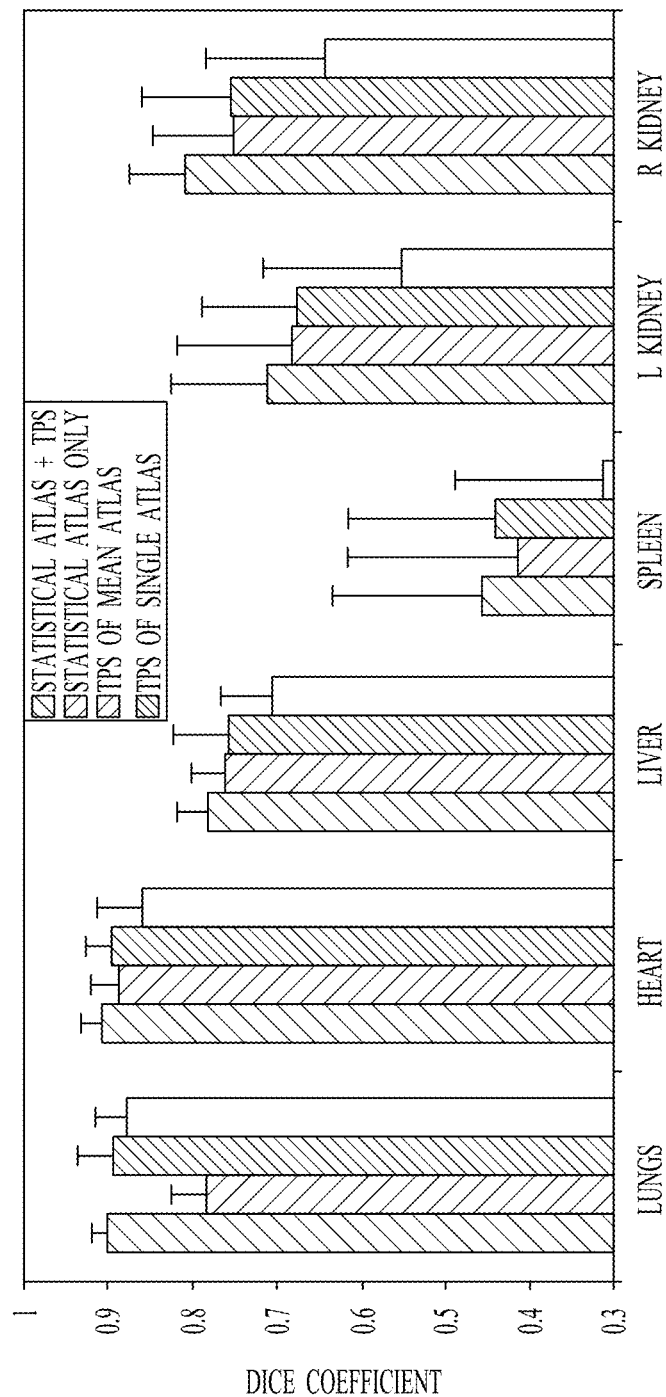

FIG. 19 is a graph comparing the organ registration accuracy (Dice coefficient) of statistical atlas registration with TPS-based deformable registration.

Figure 20:
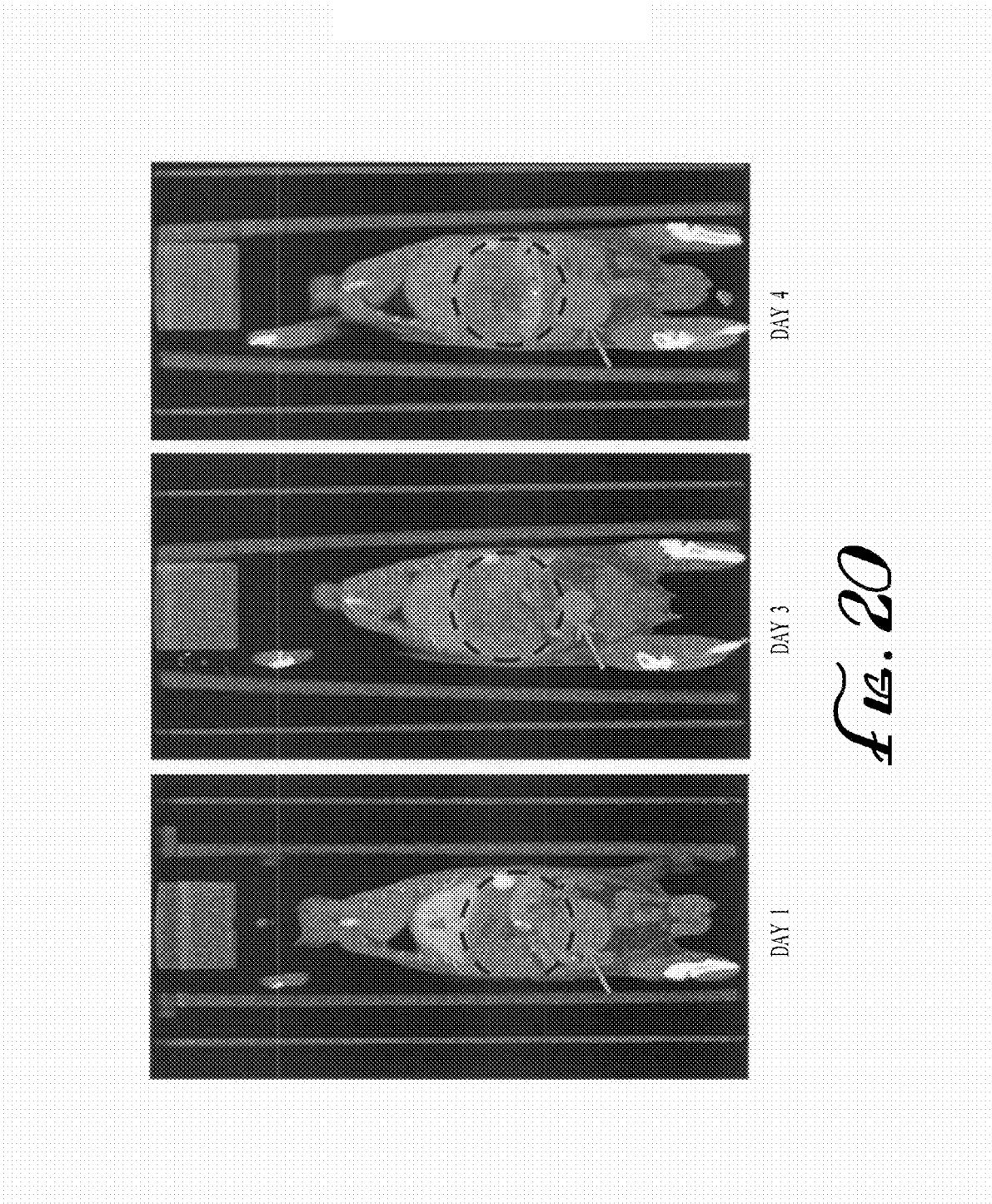

FIG. 20 is a composite image showing longitudinal micro-CT images of the same subject at day 1, day 3 and day 4 to illustrate changes in bladder position, indicated by the arrow, and size.

Figure 21A:
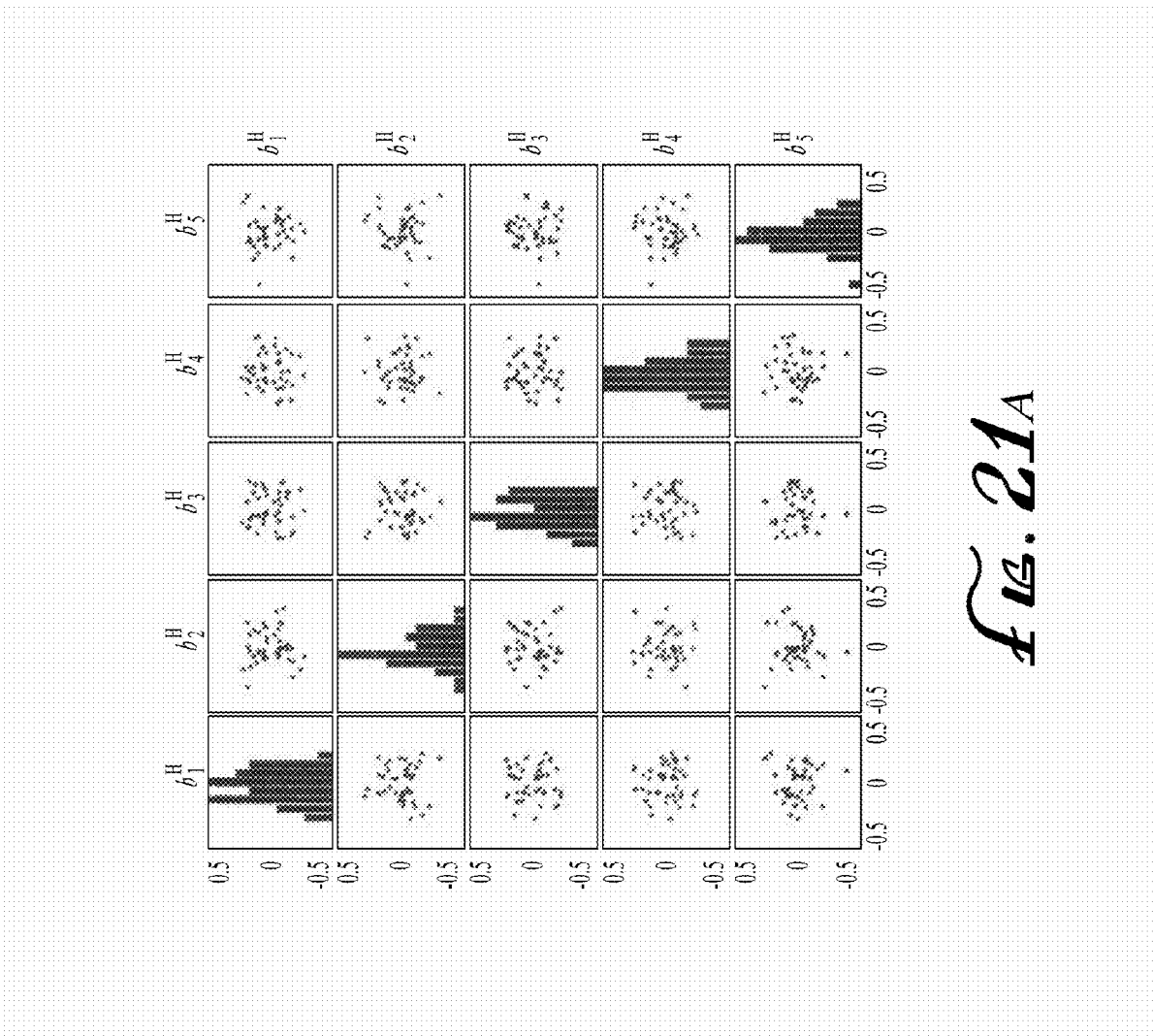
Figure 21B:
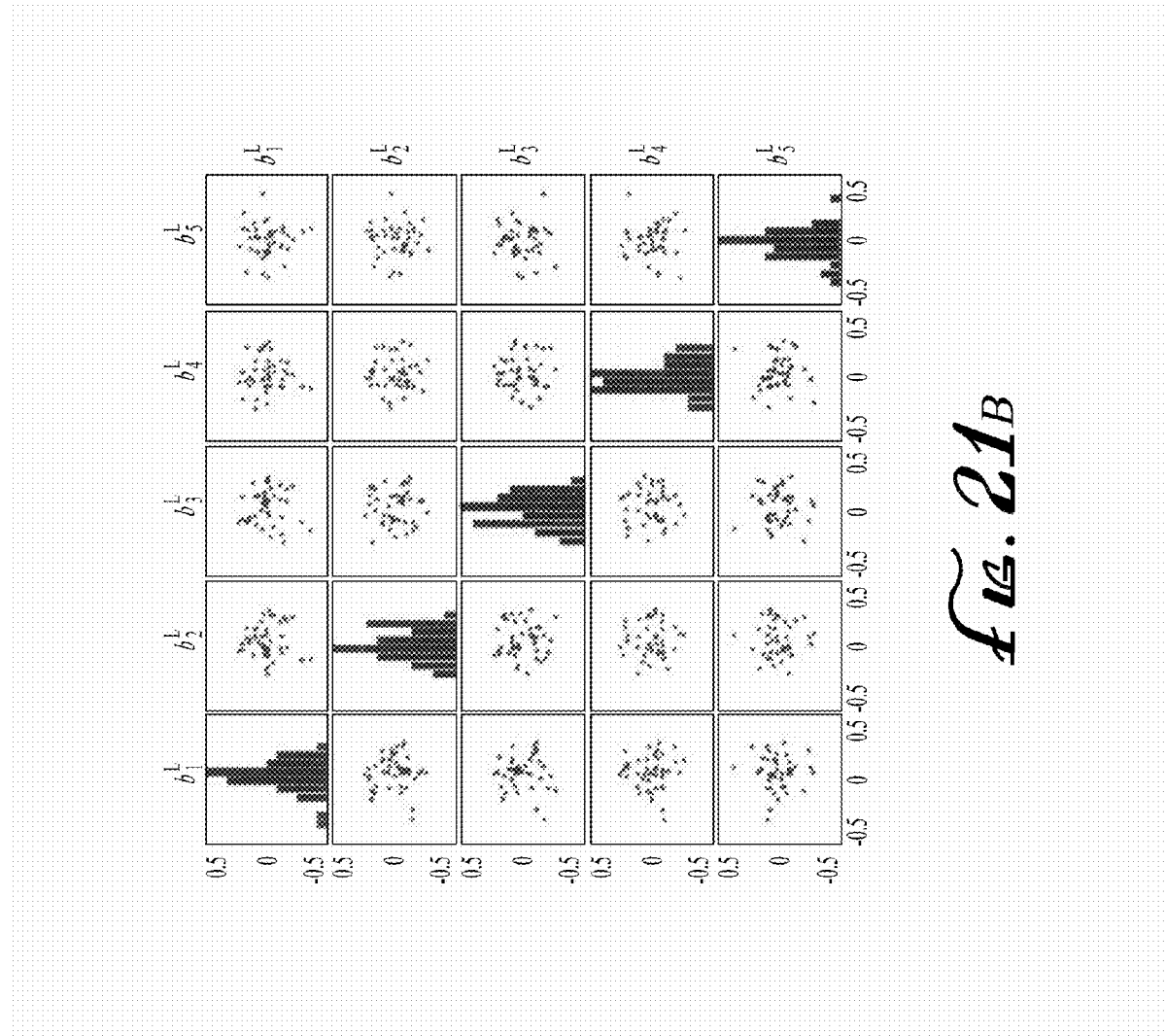

FIG. 21A shows distributions of the first five principal components of $b^H$, based on 45 subjects and FIG. 21B distributions of the first five principal components of $b^L$, plotted in the same way as FIG. 21A.

Figure 22:
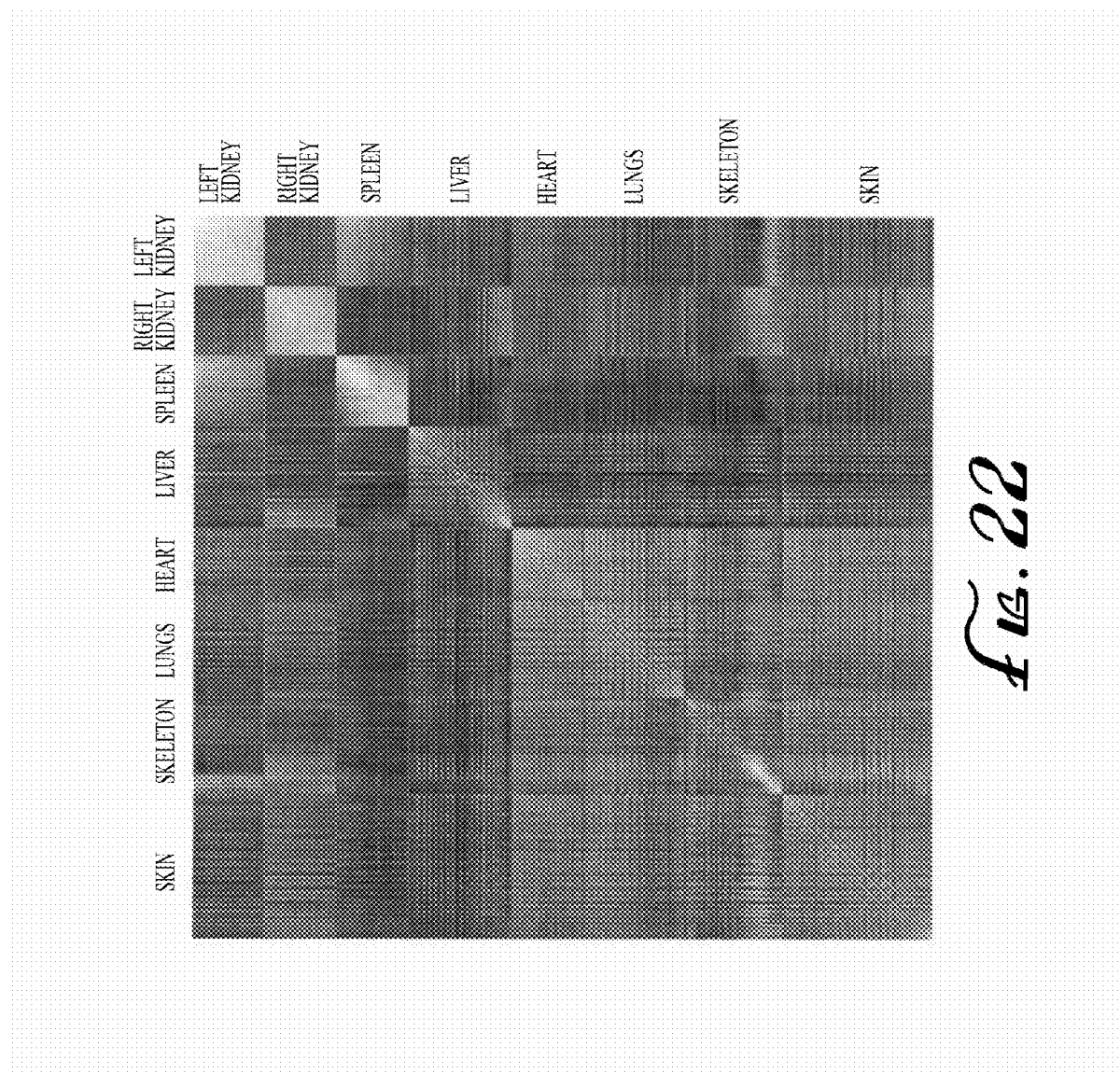

FIG. 22 is a correlation matrix of the vertex coordinates of all organs.

Figure 23:
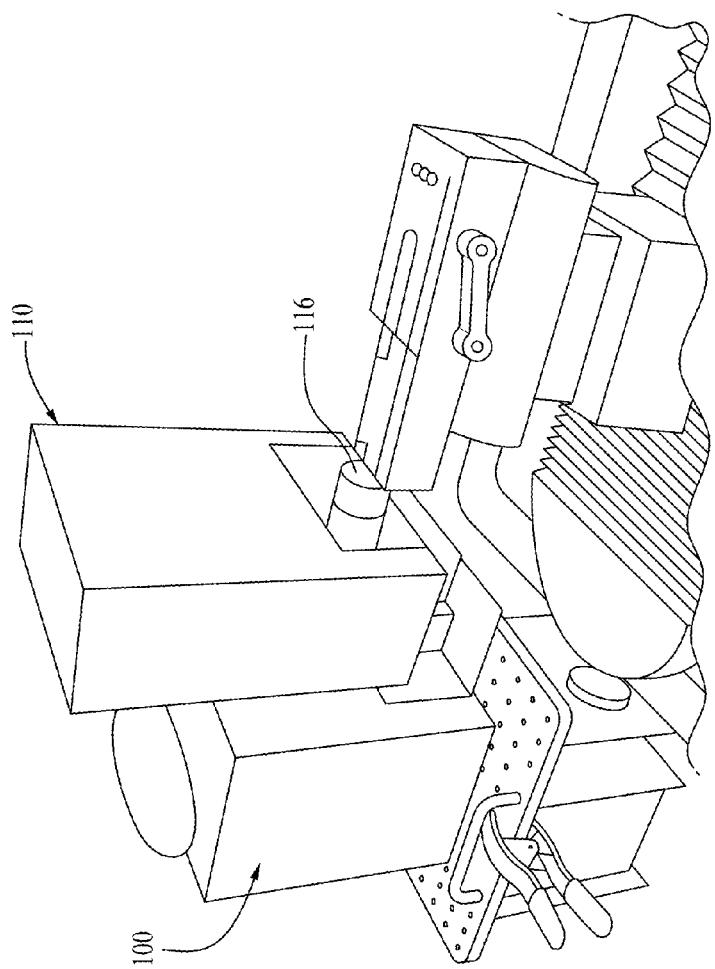

FIG. 23 is a perspective side view of an image capture system, referred to as PETbox4, incorporating features of the invention.

Figure 24:
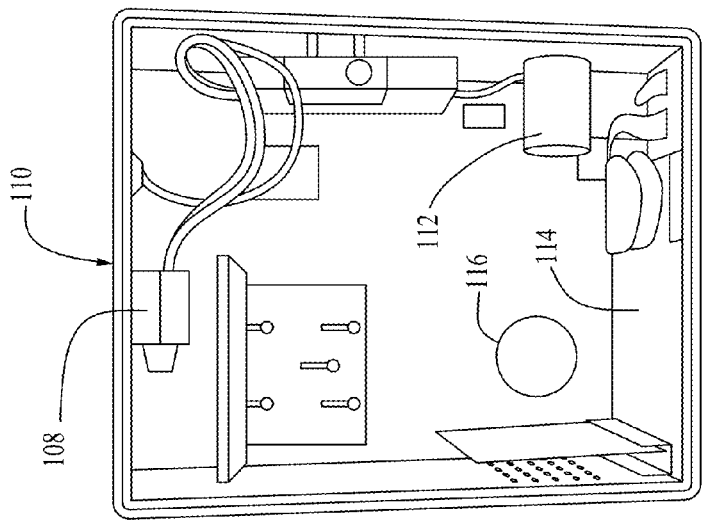

FIG. 24 is a cutaway view of the sample chamber portion of FIG. 23.

Figures 25A, 25B, 25C, 25D:
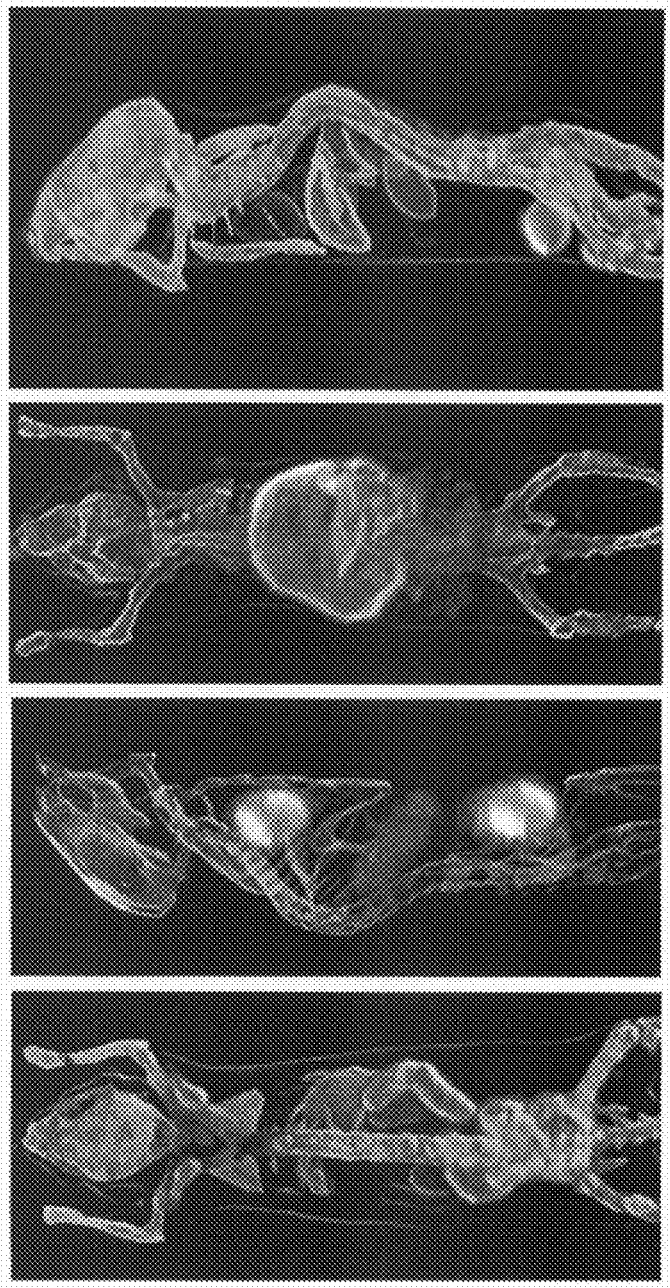

FIGS. 25A, 25B, 25C and 25D show volume PETbox4 images fused with the co-registered mouse atlases for a 10 minute acquisition for a subject labeled with 4.6 µCi F-18 labeled gene expression probe (FIG. 25A); a 30 minute scan, with a subject containing 42.4 µCi FDG FIG. 25B; a 15 minute scan, with a subject containing 11.6 µCi Cu-64 labeled antibody fragments FIG. 25C and a 20 minute scan, with a subject containing 34.1 µCi NaF (FIG. 25D).

Several of the above listed Figures are gray scale versions of images that were previously artificially rendered in color. While an observer can readily distinguish the features illustrated in the gray scale images, the colored images, copies of are available from applicants, appear in color in the following publications of Applicants, all of which are incorporated herein in their entirety by reference:

Wang, H. et al "Mouse Atlas Registration With Non-Tomographic Imaging Modalities—A Pilot Study Based On Simulation" *Molecular Imaging and Technology*, on line publication, (8 Oct., 2011) 14, No 4, (August 2012)

Wang, H, et al, "Estimation of Mouse Organ Location Through Registration of a Statistical Mouse Atlas with Micro-CT Images" *Medical Imaging, IEEE Transactions* Volume: 31, Issue: 1 p88-102, (January 2012), Published online 2011 Aug. 18, 2011 10.1109/TMI.2011.2165294, NIH Public Access Author Manuscript.

Wang, H. et al. "Registration Of A Digital Mouse Atlas With X-Ray Projection Image, Optical Camera Photo, And Laser Surface Scan", *J Nucl Med.* 2011; 52 (Supplement 1):214.

Wang, H, et al, "PETbox4: A Preclinical PET Tomograph Integrated with a Mouse Atlas Registration System" *Nuclear*

Science Symposium and Medical Imaging Conference (NSS/MIC), 2011 IEEE, Page(s): 2328-2331 (23-29 Oct. 2011

These referenced documents were all published after applicants prior filed Provisional application U.S. 61/574, 514

DETAILED DISCUSSION

In one embodiment, an atlas is registered to the non-tomographic images via an iterative process in which the atlas is projected onto one or more X-ray views, photographs, and/or other 3D surface mesh images, such as laser scans, of a subject animal. These projections are registered with the X-ray projection, optical photo and/or laser range data of the target subject, based on mutual information and B-Splines. The registration results of the non-tomographic modalities are combined into a 3D deformation which is applied to the atlas. The iteration terminates when the deformed atlas shows small enough difference between two adjacent loops.

The registration accuracy in one embodiment was evaluated by simulations using X-ray projections, optical photos and laser scans of 23 mouse subjects created from contrast-enhanced μCT images. The registration results show that bigger organs, such as whole-body, brain and liver, tend to have best accuracy, while smaller or thinner organs like spleen and skeleton tend to be less accurate.

The registration results show that this method can output useful organ approximations and provide a reasonable starting point for organ quantification. The hardware requirements for this method are lower than for fully 3D tomographic systems. FIGS. 1A-1D include 4 different images of a subject mouse with (a) being a top-view X-ray projection of the target subject, (b) being a side-view silhouette photo of the target subject, (c) being showing laser range data of the target subject and (d) showing the registration results based on the images of (a) (b) and (c). Table 1 lists several different organs and compares the accuracy of the results above described technique with the actual data in a digital atlas

TABLE 1

ACCURACY OF ORGAN COMPARISON

| | mean | Std. |
|---|---|---|
| Whole Body | 0.925 | 0.011 |
| Brain | 0.761 | 0.073 |
| Skeleton | 0.398 | 0.072 |
| Lungs | 0.589 | 0.101 |
| Heart | 0.596 | 0.111 |
| Liver | 0.588 | 0.086 |
| Spleen | 0.237 | 0.151 |
| Kidneys | 0.529 | 0.171 |

Accuracy is measured by the Dice coefficient: Dice = 2|A∩S|/|A| + |S|, (Dice∈[0, 1]), where A and S are organ regions of the registered atlas and the subject, respectively; |·|denotes the voxel number.

Currently, anatomical context is provided with tomographic x-ray CT systems that are either directly attached to the functional imaging system, or have a co-registered field of view and use specialized imaging chambers.

The 2D/3D mouse atlas registration method described herein is based on X-ray projections and optical photos. Compared to other existing mouse atlas registration methods, the atlas registration method described herein has several unique features:

1. The method only requires 2D X-ray projections and/or optical photos. No 3D tomographic acquisition is needed;
2. It allows flexible combinations of an X-ray projection and an optical photo from different view points, including "top-view X-ray and side-view photo", "top-view photo and side-view X-ray", and "top-view X-ray and side-view X-ray";
3. It is fully automatic and no user interface is required; and
4. The computational demand is reasonably low to allow high-throughput imaging. The method can be executed on a standard desktop PC within 3 minutes.

Workflow of 2D/3D Atlas Registration

Figure 2:
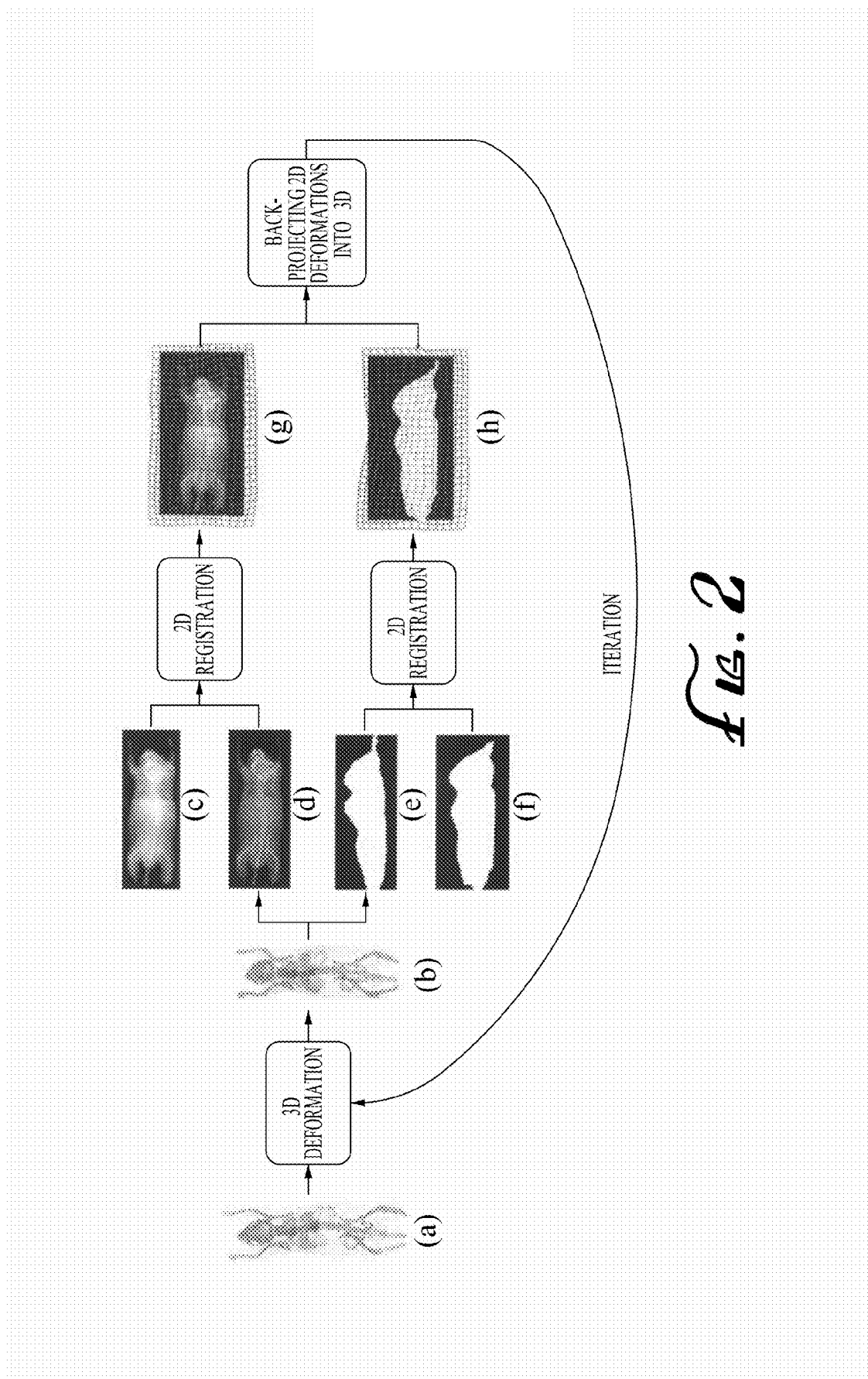
FIG. 2 illustrates the workflow procedure for the 2D/3D atlas registration with steps a)-h comprising (a). The mouse atlas. (b) The deformed mouse atlas. (c) Top-view projection of the target subject. (d) Simulated top-view projection of the deformed atlas. (e) Side-view silhouette projection of the target subject. (f) Simulated side-view silhouette projection of the deformed atlas. (g) 2D deformation obtained from top-view registration including a deformed grid and (h) 2D deformation silhouette obtained from side-view registration.

FIG. 2 shows an embodiment of the workflow procedure of the 2D/3D atlas registration method described herein. This method requires both top-view and side-view 2D images as inputs. A purpose of registration is to deform the atlas in 3D to match the target subject. The desired 3D deformation is estimated from both top-view and side-view projection images of the target subject. The term "projection images" refers to either the X-ray projection or the camera photo. For the camera photo, it is assumed to be a binary image of the body profile extracted from the optical photo of the mouse body. Note that although in FIG. 2 the "top-view X-ray and side-view camera" are used for demonstration purpose, in practice other combinations, described below, can be used, such as "top-view camera and side-view X-ray" or "top-view X-ray and side-view X-ray", as an example.

The mouse atlas was obtained by segmenting contrast-enhanced mouse micro-CT images acquired at Crump Institute for Molecular Imaging, UCLA. Major organs, including the body region, skeleton, lungs, heart, liver, spleen, kidneys and bladder were segmented from the contrast-enhanced micro-CT images. For fast registration, the segmented organs were converted into triangular surface meshes.

Before registration, the atlas is initially positioned at the same location as the target subject, based on the assumption that the 3D position of the target subject is known from the hardware setup. The 3D deformation is estimated via an iterative process. The initial assumption is that the deformation is zero, i.e. no deformation. At each iteration, the deformed atlas (FIG. 2, step (b)) is projected into 2D images of top-view (FIG. 2 step (d)) and side-view (FIG. 2 step (f)), via a simulation projection method which is described below. The top-view and side-view projection images of the atlas are registered with the top-view (FIG. 2 step (c)) and side-view (FIG. 2 step (e)) projection images of the target subject, respectively. 2D deformations of both top-view (FIG. 2 step (g)) and side-view (FIG. 2 step (h)) are obtained from the registrations. The two 2D deformations are back-projected into 3D deformation. Then the atlas is deformed again and enters the next iteration step. The iteration terminates when the deformed atlas shows small enough difference between two iteration steps, i.e.

$$D_{atlas} < \epsilon, \quad (1)$$

where $$D_{atlas} = \operatorname*{mean}_{i}(v_i^{k+1} - v_i^k),$$

$v_i^k$ represents the coordinate of the $i^{th}$ surface vertices of the atlas at iteration k, and c is empirically set as 0.1 mm.

For both top-view and side-view, the projection images are registered using the same 2D registration method, i.e.

B-spline based registration using advanced mattes mutual information as similarity metric. The size of the B-spline control grid is 10×10 pixels. A multi-resolution registration scheme is used to accelerate the registration. Five levels of spatial resolution are used. The down-sampling ratios for the five resolutions are 16, 8, 4, 2 and 1. An adaptive stochastic gradient descent algorithm is used for optimization of each resolution.

The simulation based on projection of X-ray and camera images, as well as the back-projection of 2D deformations into 3D are described in detail below.

Simulation Projection of X-Ray and Camera for the Mouse Atlas

Figure 3B:
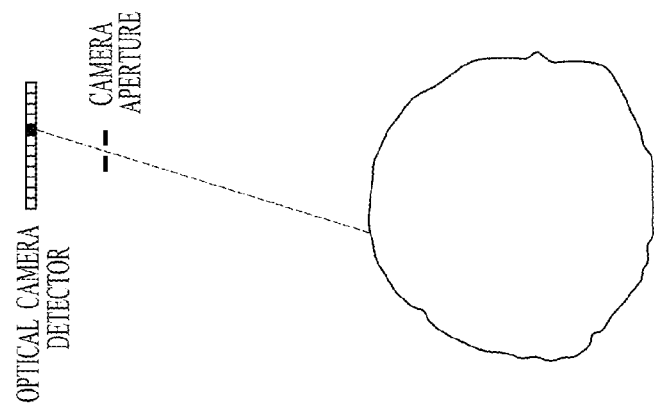
FIG. 3B shows a simulated camera projection of the mouse atlas.
Figure 3A:
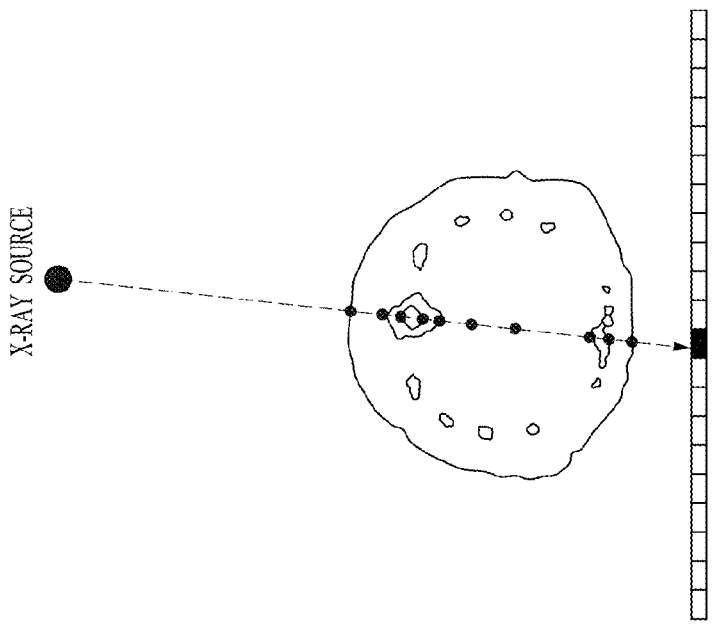
FIG. 3 A schematically illustrates a simulated X-ray projection of the mouse atlas.
FIGS. 13A, 13B and 3C illustrate the shape variations generated from the statistical shape models and the conditional Gaussian model where

The simulation using X-ray projections for the mouse atlas is shown by FIGS. 3A and 3B. In FIG. 3A the simulation X-ray point source and pixilated detector are located at opposite sides the digital mouse atlas. The settings of the X-ray system, including the relative positions of the source and the detector, as well as the detector size and pixel resolution, are all the same with the real physical X-ray system used for imaging the target subject. An X-ray is emitted from the source into 3D space. When the X-ray intersects with the organ surface of the mouse atlas, the intersection points are recorded (shown as the enlarged dots in FIG. 3A). The X-ray line is divided by the intersection points into several sections, with each section inside a particular tissue. The pixel that receives this X-ray is assigned with the value of $$I = S \cdot \exp\left(-\sum_i \mu_i l_i\right), \quad (2)$$

where I is the pixel value, S is the source energy, i denotes the section id, l is the length of the X-ray section and μ is the tissue attenuation coefficient. For a more rapid simulation, only three organs, the body surface, the bones and the lungs, are shown: X-ray sections inside body surfaces, bones and lungs are attenuated with μ of water, bone and air, respectively. Other organs are not considered in the simulation because in practice they have attenuation coefficients similar to water.

The simulation using the camera projection is shown in FIG. 3B. Settings of the simulation camera system, including the relative positions of the aperture and the detector, as well as the detector size and pixel resolution, are all the same with the real physical camera for imaging the target subject. Only the body surface of the mouse atlas is used for the optical image simulation. For each detector pixel, a straight line is made to connect the centers of the pixel and the camera aperture. If this line intersects with the atlas surface, the pixel is assigned with value 1, otherwise assigned with value 0. This simulation will generate a binary image of the projected mouse profile.

While FIGS. 3A and 3B demonstrate the principles in top-view, the same principles also apply to the side-view.

Back-Projecting 2D Deformations into 3D

FIGS. 4A and 4B demonstrate back-projections of 2D deformation for the top-view and side-view, respectively where p is an arbitrary vertex of the atlas surface mesh, p' is the projection point of p onto the detector (either X-ray detector or camera detector), and s is the X-ray point source or camera aperture. The 3D deformation is characterized by the coordinate system (x, y, z), and the 2D deformation is characterized by the coordinate system (m, n). The 2D deformation vector of p' is defined as $v(p')=[v_m(p'), v_n(p')]$.

Note for the camera projection, the 2D coordinate axes are in opposite directions of their corresponding 3D coordinate axes, because the pinhole projection generates inverse images.

For the top-view projection, $v^T(p)=[v_x^T(p), v_y^T(p), v_z^T(p)]$ is used to denote the 3D deformation vector. $v^T(p)$ is back-projected from the v(p') using $$v_x^T(p) = \frac{|sp|}{|sp'|} v_m(p') \quad (3)$$
$$v_y^T(p) = \frac{|sp|}{|sp'|} v_n(p')$$
$$v_z^T(p) = 0$$

where |sp| and |sp'| are the distances from s to p and p', respectively.

For the side-view projection, $v^S(p)=[v_x^S(p), v_y^S(p), v_z^S(p)]$ is used to denote the 3D deformation vector. $v^S(p)$ is back-projected from the v(p') using $$v_x^S(p) = 0 \quad (4)$$
$$v_y^S(p) = \frac{|sp|}{|sp'|} v_n(p')$$
$$v_z^S(p) = \frac{|sp|}{|sp'|} v_m(p').$$

The back-projections of equation (3) and (4) preserve the collinearity of all the points in line sp' after the 3D deformation. They therefore guarantee that the deformed atlas can generate the deformed projection images. The top-view and side-view deformations are combined together as $$v_x(p) = v_x^T(p) \quad (5)$$
$$v_y(p) = \frac{1}{2}(v_y^T(p) + v_y^S(p))$$
$$v_z(p) = v_z^T(p),$$

where $v(p)=[v_x(p), v_y(p), v_z(p)]$ is the combined 3D deformation of the atlas.

Results of 2D/3D Atlas Registration

This method was tested based on the use of X-ray and camera systems. 23 mouse phantoms were created by doing organ segmentation with contrast-enhanced micro-CT images. The same method of subsection C2 was used to generate X-ray and camera projection images from the mouse phantoms. The point identified as s represents the X-ray source or the camera aperture, and c is the center of detector plane; the phantom center o was chosen as the origin of the 3D coordinate space. The point s was located at [0,0,156] mm and [156,0,0] mm for top-view and side-view, respectively. The length of |sc| was set as 208 mm and 3 mm for X-ray and camera, respectively. The size of the X-ray detector was 140×50 mm, with pixel matrix size 248×128. The size of the camera detector was 4.5×3.4 mm, with pixel matrix size 640×480.

Three different combinations of X-ray and camera projections were tested based on the system described above. These combinations were "top-view X-ray and side-view camera", "top-view camera and side-view X-ray", and "top-view X-ray and side-view X-ray". The 2D/3D registration was performed for each combination. The registration time for each combination was ≈130 sec based on a PC of 3.05 GHz CPU and 5.99 GB RAM.

FIG. 5 illustrates typical results for the three combinations based on two test subjects. FIG. 5 shows 2D/3D atlas registration results based on test images. Three different combinations of X-ray and an optical camera were utilized, i.e. "top-view X-ray and side-view camera", "top-view camera and side-view X-ray", and "top-view X-ray and side-view X-ray". This figure shows the registration results of the three combinations based on two test subjects. It can thus be observed that the use of X-ray projection improves the registration accuracy of X-ray-visible organs (such as skeleton and lungs). However, the use of X-ray projection makes the registration focus more on X-ray-visible organs, and therefore biases the matching of X-ray-invisible organs (such as liver, spleen and kidneys). Among the three combinations, "top-view X-ray and side-view photo" tends to achieve the best trade-off between the X-ray-visible organs and X-ray-invisible organs.

Based on the above results, the evaluation was expanded to encompass eleven combinations of three non-tomographic imaging modalities. The registration accuracy of each combination was evaluated. Different atlases were created based on five distinct subjects to evaluate the influence of the atlas on registration accuracy. As discussed below, by comparing the eleven combinations, the top-view x-ray projection combined with the side-view optical camera yielded the best overall registration accuracy of all organs. The use of a surface scanner improved the registration accuracy of skin, spleen and kidneys. The evaluation of different atlases revealed that choosing an atlas similar to the anatomy of the subject population is important for improving the registration accuracy.

Mouse atlas registration with different combinations of three non-tomographic imaging modalities, including an optical camera, a surface scanner and a planar X-ray projector that registers the mouse atlas to different combinations of these three modalities, has thus been demonstrated along with the registration accuracy of the different combinations. The x-ray projections, optical or digital images and scans to produce the simulation combination are obtained substantially simultaneously, sequentially or in overlapping time periods.

Creation of Mouse Atlases and Subject Phantoms

The atlases described herein were created from 28 contrast-enhanced mouse micro-CT images, which were selected from the pre-clinical imaging database of the Crump Institute for Molecular Imaging, UCLA. The contrast agent was Fenestra™ LC (ART, Quebec, Canada). The images were acquired in vivo with healthy subjects of different strains, weights, postures and sex. The three most frequently used strains (Nude, C57, and severe-combined immunodeficient (SCID)) were included. The body weights ranged from 15 g to 30 g. The imaging system was a MicroCAT II small animal CT (Siemens Preclinical Solutions, Knoxville, Tenn., USA) and the images were reconstructed using a modified Feldkamp algorithm with isotropic voxel size 0.20 mm, and matrix size 256×256×496.

Contrast-enhanced CT images were used to provide definition of organ regions and to facilitate the evaluation of registration accuracy. Major mouse organs were segmented from the 28 images by individuals using a computer-assisted segmentation tool which incorporated the methods of intensity thresholding, region growing, deformable simplex mesh and graph cuts. The segmented organs included skin, skeleton, heart, lungs, liver, spleen, kidneys and bladder.

Figure 6:
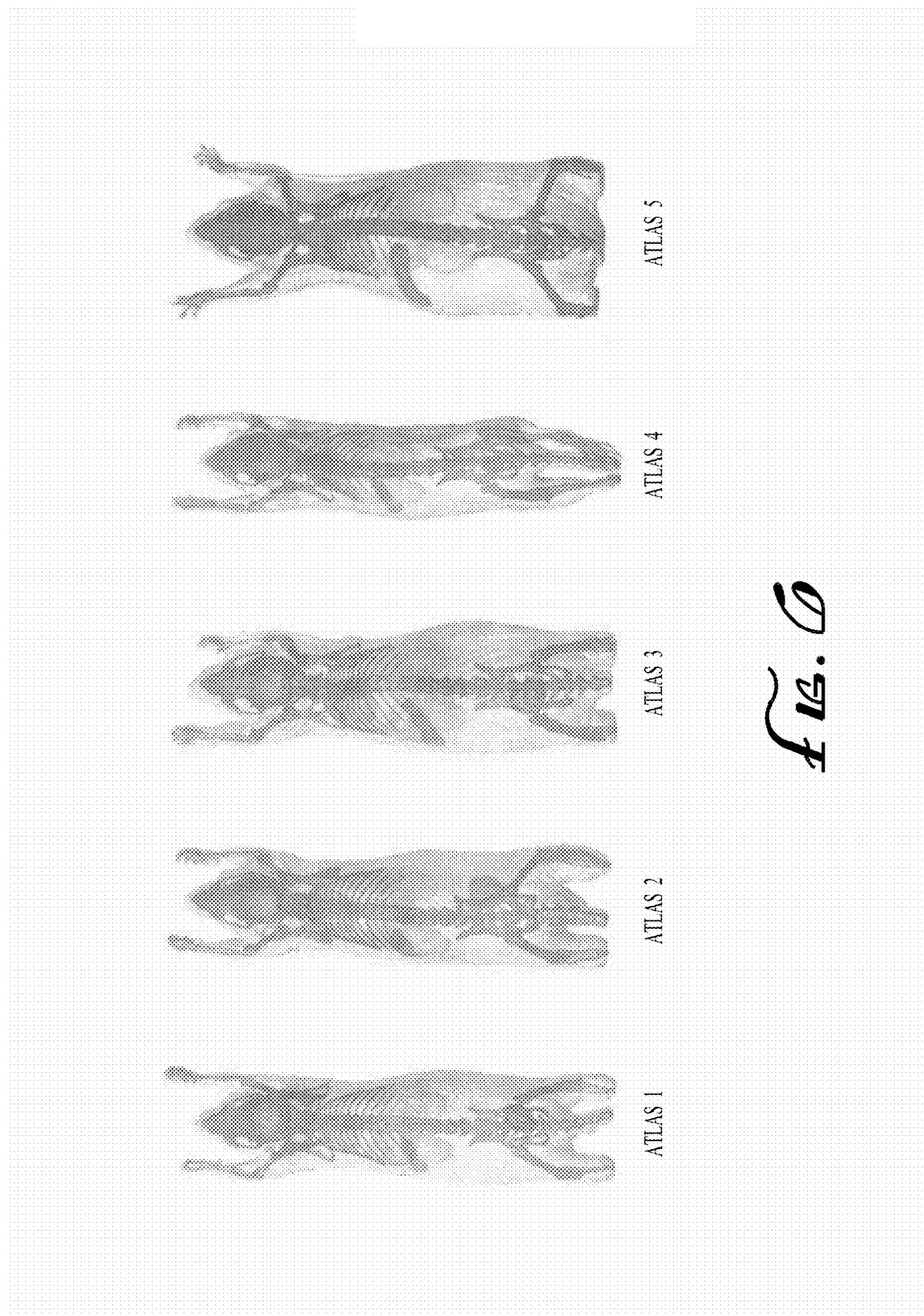
FIG. 6. illustrates five mouse atlases labeled atlas 1-atlas 5, created from contrast-enhanced micro-CT images.

Five of the 28 images were chosen as mouse atlases (shown in FIG. 6 as atlas 1-atlas 5), the remaining 23 were used as target subjects. The five atlases were chosen to represent different sub-groups of the 28 images in terms of body shape and organ anatomy. The reason for selecting multiple atlases was to evaluate the influence of atlas choice on the registration accuracy. For this reason atlases were created rather than using the limited number of currently available whole-body mouse atlases.

Simulation Using Three Non-Tomographic Modalities

Figure 7:
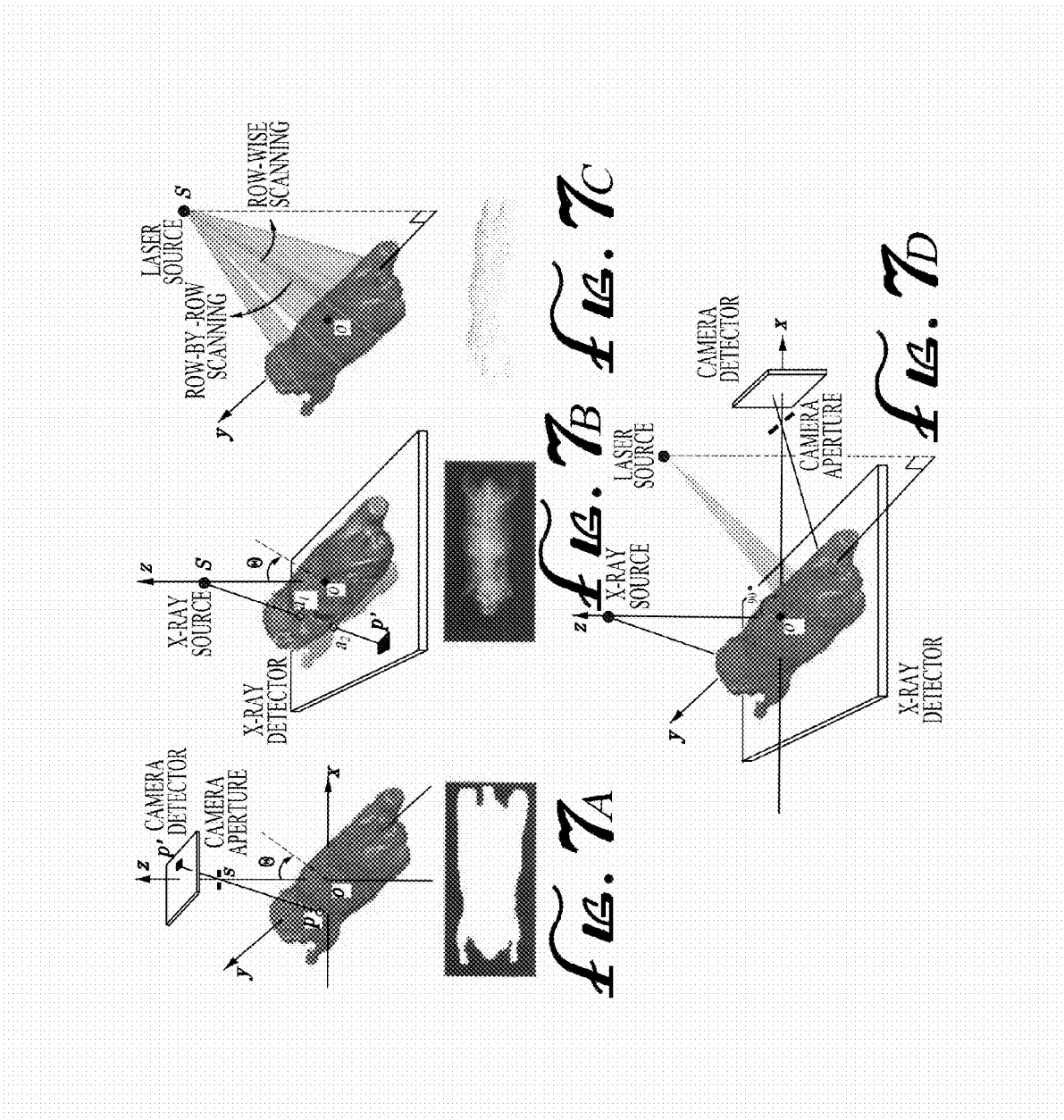
FIGS. 7A-7D show three simulation configurations and the results of the three non-tomographic modalities where

Optical photographs, X-ray projections and surface scans were acquired based on the 23 subjects. FIGS. 7A, 7B, and 7C demonstrate the simulation configurations and results for the three modalities. To represent the common field of view of the three modalities, a 3D global world coordinate system was defined (FIG. 7A with the origin located at the geometric center of the subject image. The x, y and z axes are defined to point from left to right, tail to head, and anterior to posterior of the subject, respectively. FIG. 7D shows a combination of the three modalities, with X-ray and surface scan top-views and photo camera side-views. Many other combinations can be achieved with these non-tomographic imaging modalities. Obtaining all the combinations by hardware is nontrivial and therefore they were validated using various simulation approaches. This way the different combinations can be compared using exactly the same test datasets.

The simulation using the optical camera is based on the pinhole projection model (FIG. 7A. The principal axis (the line connecting the detector center and the camera aperture) of the camera is defined to belong in the xoy plane and pass through the origin o. The principle axis can be rotated along the y axis by different view angles θ denotes the view angle; accordingly θ=00 represents a top-view and θ=90° represents a side-view. The camera detector is 156 mm away from the origin o. In this example, the focal length is 3 mm and the detector size is 4.5×3.4 mm, with a 640×480 pixel matrix. For an arbitrary pixel p' in the detector, a straight line is drawn connecting the center of the pixel and the geometric camera aperture s. If this line intersects with the subject surface, the pixel is assigned value 1, otherwise it is assigned a 0 value. The simulation produces a binary silhouette image of the mouse body, as shown at the bottom of FIG. 7(a). This result is slightly different from a real-world photo which is a gray-scale or RGB-color picture of the mouse body. For a real-world photo, an additional segmentation step is required to extract the body silhouette.

The simulation using the x-ray projection is shown in FIG. 7B. The x-ray point source and the pixelated detector are located at opposite sides of the mouse body. The principal axis (the line connecting the detector center and the point source) is defined to belong to the xoy plane and pass through the origin o. The principle axis is allowed to rotate along the origin for projections by different view angles. The view angle θ is defined in the same manner as above for the optical camera. The distance from the point source to the origin is 156 mm, and the distance from the detector center to the origin is 52 mm. The size of the x-ray detector is 100×50 mm, with a pixel matrix size of 248×128. For an arbitrary pixel p' in the detector, a straight line is drawn connecting the centers of the pixel and the point source s. If this line intersects with the subject surface at points $a_1$ and $a_2$, the pixel p' is assigned the value $$I = I_0 \cdot \exp[\int_{a_i}^{a_2} \mu(s) ds] \quad (6)$$

where I is the pixel value, $I_0$ is the source energy, $\mu(s)$ is the linear tissue attenuation coefficient along the emitted x-ray, and $\int_{a_i}^{a_2}$ ds denotes the line integration along the emitted x-ray. The coefficient μ(s) can be obtained from the CT image that was used for simulating the subject. Since the CT-images are contrast-enhanced, the voxel intensities will not exactly reflect the tissue attenuation coefficients in the non-contrast-enhanced mouse projection images that we anticipate. To eliminate the influence of contrast agent, the voxel intensities of contrast-enhanced organs (the liver and spleen which were already segmented) are scaled down to the level of brain intensity. The simulation x-ray projection image is shown at the bottom of FIG. 7B, with an inverse intensity map.

The simulation using the surface scanner is shown in FIG. 7C. There are several types of surface scanners, such as laser scanner, structured light scanner and swept plane scanner. All of these are based on a similar imaging geometry as described by Douglas, L and Gabriel, T ("Build your own 3D Scanner: 3D Photography for beginners" In: the ACM SIGGRAPH 2009 Courses, New Orleans, La.: ACM), incorporated herein in its entirety by reference. The laser scanner was simulated, but the same registration approach can also be applied to other types of scanners. The laser source is located at position (0, −60, 156) mm of the world coordinate system. The laser is emitted from the source and is scanned in a row-by-row manner parallel to the x axis. If the laser line intersects with the body surface, the intersection point is recorded. The final range data are composed of all the intersection points of the scanning, as shown at the bottom of FIG. 7D. The resulting range data reveals the shape of the upper body surface, but the bottom surface is missing.

Different Combinations of the Three Non-Tomographic Modalities

Figure 9:
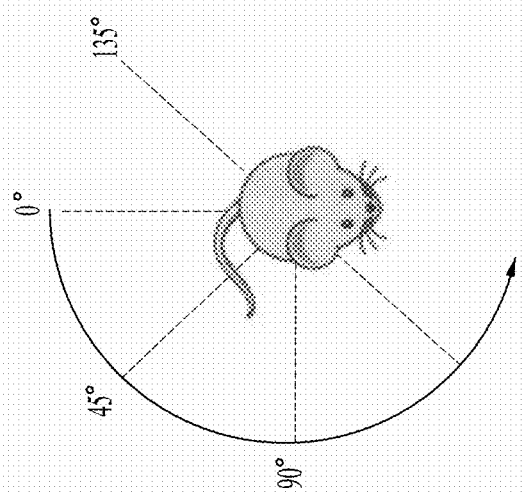
FIG. 9 is a schematic representation of a subject mouse showing the various angles used to generate images which are combined to produce the 3D image.

In practice, the three non-tomographic imaging modalities can be combined in various different ways. One of the possible combinations is shown in FIG. 7D where the X-ray system and camera system are located at orthogonal views (θ=0° and θ=90', respectively). Eleven (11) simulation combinations were evaluated to determine which combination provides the best overall registration accuracy. "Modality θ" is used to describe the modality and view angle, where 'X', 'C' and 'L' stand for x-ray, camera and laser scan, respectively. For example, "C0" means top-view camera, and "X45" means x-ray projection from θ=450. With reference to FIG. 9, the 11 evaluated combinations are C0+C90, C0+X90, X0+C90, X0+X90, X45+X135, L Only (laser scan only), C90+L, X0+L, X90+L, X0+X90+L AND X0+C90+L as described in Table 2. The laser scanner is not necessarily located orthogonal.

TABLE 2

ELEVEN SIMULATION COMBINATIONS OF NON-TOMOGRAPHIC MODALITIES.

| | Combination | Explanations |
|---|---|---|
| 1 | C0 + C90 | The combination based on two orthogonal optical cameras. |
| 2 | C0 + X90 | Top-view optical camera and side-view x-ray projector. |
| 3 | X0 + C90 | Top-view x-ray projector and side-view optical camera. |
| 4 | X0 + X90 | Two orthogonal X-ray projectors. |
| 5 | X45 + X135 | Two oblique orthogonal X-ray projectors. |
| 6 | L Only | Laser scanner only. |
| 7 | X0 + L | Top-view X-ray projection and laser scanner. |
| 8 | X90 + L | Side-view x-ray projection and laser scanner. |
| 9 | C90 + L | Side-view optical camera and surface scanner; Note that "C0 + L" was not simulated because both "C0" and "L" are both from top-view, and therefore present redundant projections. |

TABLE 2-continued

ELEVEN SIMULATION COMBINATIONS OF NON-TOMOGRAPHIC MODALITIES.

| | Combination | Explanations |
|---|---|---|
| 10 | X0 + X90 + L | Two orthogonal x-rays and laser scanner. |
| 11 | X0 + C90 + L | The combination of top-view x-ray projection, side-view optical camera and surface scanner. |

Atlas Registration Workflow

Figure 8:
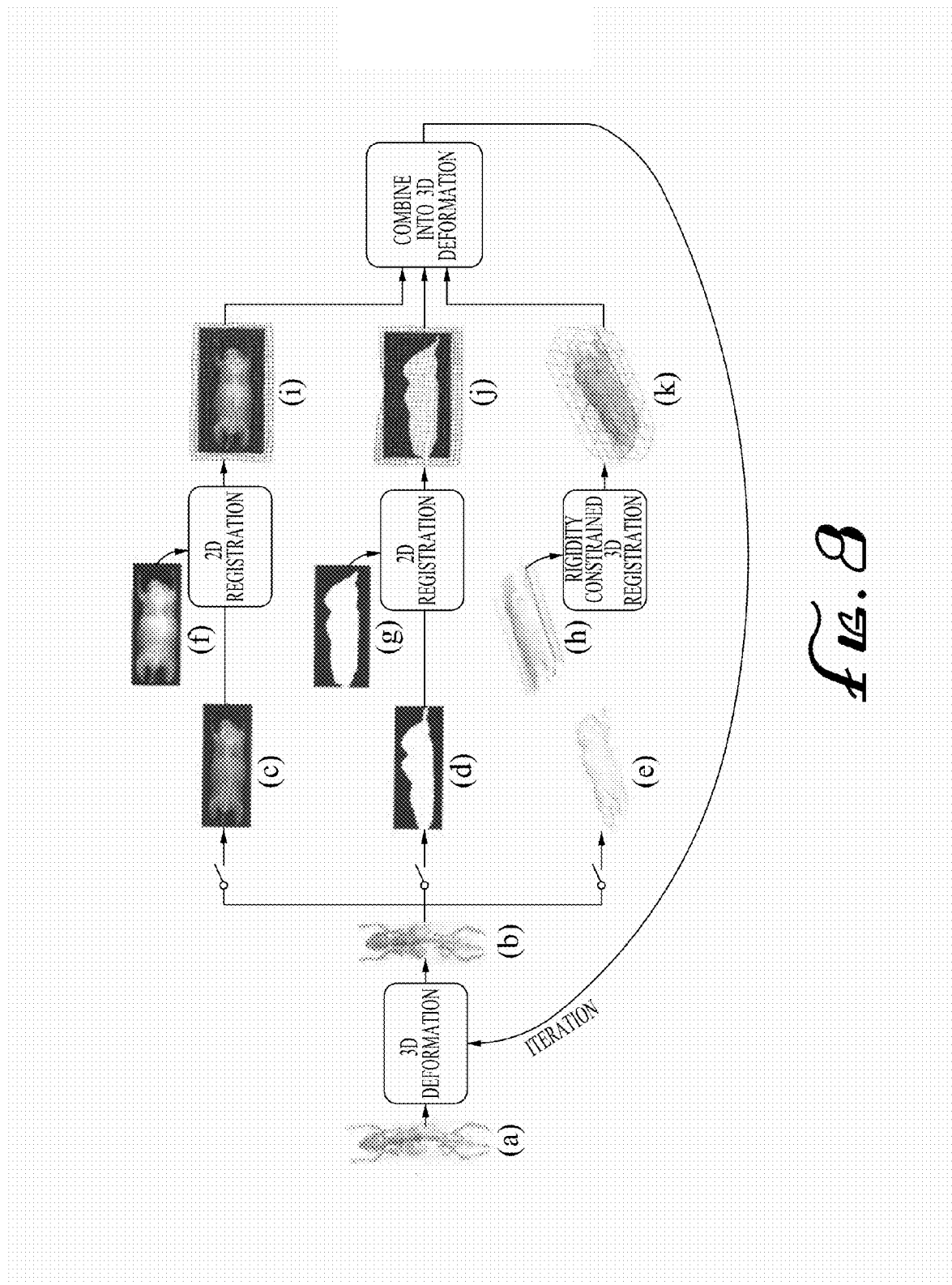
FIG. 8 illustrates an alternative to FIG. 2 for the workflow procedure for atlas registration with non-tomographic modalities with steps a)-k) where (a) is the mouse atlas to be registered, (b) is the mouse atlas deformed by 3D deformation, (c) is a virtual X-ray projection of the deformed atlas, (d) is a virtual optical photo silhouette of the deformed atlas, (e) is the body surface of the deformed atlas; (f) is an X-ray projection of the target subject, (g) is an optical silhouette photo of the target subject, (h) is a laser scan of the target subject, (i) is a 2D registration result of the X-ray projection, where the resultant 2D deformation is displayed as a deformed 2D grid, (j) is the 2D registration result of the optical photo silhouette and (k) is the 3D registration result of the body surface.

The overall method described here is designed to register one or more existing mouse atlases to different combinations of the three non-tomographic modalities. FIG. 8 demonstrates the workflow of an embodiment of this method. Three registration paths are designed for the three projection imaging modalities. The switch at the beginning of each path allows flexible combinations of the three modalities. Registration paths are shown for three modalities. A switch at the beginning of each path enables the flexible combination of different modalities. Note that although FIG. 8 demonstrates top-view X-ray and side-view camera, in practice the X-ray and cameras can also be placed at other view angles. Referring to FIG. 8, the mouse atlas to be registered step (a) is deformed by 3D deformation techniques step (b). Step (c) is a virtual X-ray projection of the deformed atlas, step (d) is a virtual optical photo silhouette of the deformed atlas, and step (e) shows the body surface of the deformed atlas. Step (f) shows an X-ray projection, step (g) shows an optical photo silhouette and step (h) shows a laser scan of the target subject, respectively. Step (i) is a 2D registration result of the X-ray projection, where the resultant 2D deformation is displayed as a deformed 2D grid. Step (j) is the 2D registration result of the optical photo silhouette and step (k) is the 3D registration result of the body surface. In step (k) the registered atlas surface is displayed along with the subject laser scan, and the resulting 3D deformation is displayed as a deformed 3D grid. Note that for demonstration purposes FIG. 8 shows a top-view x-ray projection and side-view camera photo. However the x-ray projection and camera photo can be taken from other view angles as well.

Before registration, the atlas is initially positioned at the same location as the target subject, based on the assumption that the 3D position of the target subject is known from the hardware setup such as the embodiment shown in FIGS. 23 and 24. To accelerate registration, the organs of the atlas are converted into triangular surface meshes. A purpose of the registration is to deform the atlas in 3D space to match the x-ray projection, optical silhouette and/or surface scan of the subject. The desired 3D deformation is estimated using an iterative process, with an initial assumption of no deformation. In each iteration, the deformed atlas (FIG. 8 step (b)) is virtually projected into the x-ray image (FIG. 8 step (c)), optical photo silhouette (FIG. 8 step (d)), and/or body surface mesh (FIG. 8 step (e)). These virtual projections are registered with their measured counterparts of the subject. FIG. 8 step (i) and step (j) show the 2D registration results of the x-ray projection and optical silhouette; the resulting 2D deformations are displayed as deformed grids. FIG. 8 step (k) shows the registered atlas surface with the laser scan of the subject. The resulting 3D deformation is displayed as a 3D grid The registration results of different modalities are combined to one 3D deformation, which is then applied to the atlas again. The iteration terminates when the deformed atlas shows only an acceptably small difference between two adjacent loop steps, i.e. $D_{atlas} < \epsilon$, where $$D_{atlas} = \underset{i}{\text{mean}}(v_i^k - v_i^{k-1}),$$

where $v_i^k$ represents the coordinate of the $i^{th}$ surface vertex of the atlas at iteration k, and $\epsilon$ is set as 0.2 mm, which is the voxel size of subject image.

The following description explains the details of an embodiment of the registration method for each modality, as well as the combination of the results from the different modalities into one 3D deformation.

2D Registration of Planar X-Ray and Optical Photo

In each iteration, the corresponding optical silhouette and/or x-ray projection of the atlas is generated and registered with the measured optical silhouette and/or x-ray projection of the subject. The optical silhouette of the atlas is generated in the same way as in the simulation of the optical silhouette of the subject animal. The configuration settings of the virtual camera for the atlas, including the relative positions of the aperture and the detector as well as the detector size and pixel resolution, are all the same as for the camera system of the subjects. The x-ray projection of the atlas is generated in a similar way as the simulation using the subject x-ray projection, the major difference being that the atlas x-ray projection simulation is based on a surface mesh rather than a CT volume. The registration can be accelerated using surface-based projection because surface-based projections are much faster than volume-based projection.

The configuration settings of the virtual x-ray system for the atlas, including the relative positions of the source and the detector, and the detector size and pixel resolution, are all the same as those of the real x-ray system for the subjects. A set of virtual x-rays is emitted from the source in a raster scanning fashion towards the detector pixels. If the x-ray intersects with the triangular patches of the organ mesh, the intersection points are recorded. The virtual x-ray is then cut into several sections by the intersection points, with each section inside a particular tissue. The detector pixel that receives this x-ray is assigned with the value of $$I = I_0 \cdot \exp\left(-\sum_i \mu_i l_i\right) \quad (7)$$

where I is the pixel value, $I_0$ is the source energy, i denotes the index of x-ray section, l is the length of the x-ray section and $\mu$ is the tissue attenuation coefficient. Only the body surface, the bones and the lungs are used for the projection. The x-ray sections inside the body surface, bones and lungs are attenuated with $\mu$ of water, bone and air, respectively. Other soft organs are not considered assuming they have attenuation coefficients similar to water. FIG. 8 step (c) shows the surface-based x-ray projection of the atlas, which roughly resembles the volume-based projection (FIG. 7B).

Both x-ray projection images and optical photos are registered using the same 2D registration method, i.e. B-spline registration based on mutual information. This method is implemented using the Elastix™ software, which incorporates a family of state-of-the-art image registration methods. The size of the B-spline control grid is 10×10 pixels. A multi-resolution registration scheme was used to accelerate the registration. Five levels of resolutions were used. The down-sampling ratios for the five resolutions are 16, 8, 4, 2 and 1. An adaptive stochastic gradient descent algorithm was used for the optimization at each resolution.

Rigidity-Constrained Registration of the Body Surface

Atlas registration with a laser scan presents a problem due to the possibility of incomplete the scan data. Furthermore, since the laser does not penetrate the mouse body, the bottom surface of the subject is missing. To address this problem, the shape of the mouse bed was used to emulate the bottom surface of the subject, under the assumption that the lower mouse surface conforms well to the supporting bed. This assumption is reasonable for in vivo imaging because the bottom of a living mouse is soft enough to conform to the bed shape. For this procedure to simulate images, the scan of the bed was obtained by using the laser scan on the bed segmented from the contrast-enhanced CT image. For physical imaging systems with reliable reproducibility of bed placement, the scan of the bed only needs to be performed once and will be consistent for different subjects. After the bed is scanned, the subject is also scanned along with the bed. The overlapping points of the two scans were removed leaving only non-overlapping parts that enclose the body surface.

To register the atlas surface point set to the enclosed laser scan point set, the rigidity-constrained deformable registration method shown in Staring, M, Klein, S and Pluim, J P "A Rigidity Penalty Term For Nonrigid Registration". *Med. Phys.* 34: p4098-4108, (2007), incorporated herein in its entirety by reference, is used. The method assigns different organs of the atlas with different rigidity values, so as to prevent implausible deformation of the organ shapes during the registration. For example, the rigidity values for different organs are 0.01 for body, bones and bladder, 0.1 for lungs, heart, liver and spleen, 0.8 for kidneys and 0.9 for the whole head. Three dimensional distance maps of the two point sets were computed as the input images of the registration method. The rigidity-constrained registration was performed using the Elastix™ software. The spatial transformation model is B-spline deformation, and the final control grid size is 8×8×8 voxels. The image similarity metric is advanced mean squared difference, and the optimizer is an adaptive stochastic gradient descent algorithm. A four-level multi-resolution strategy was used, and the down-sampling ratios for the four resolutions were 8, 4, 2 and 1.

Combining the Registration Results of Different Modalities

Because the atlas is registered separately to different modalities, the registration of each modality yields a separate spatial deformation. 2D registrations (x-ray projection or optical photo) yield 2D deformations (FIG. 8 step (i) and (j)) while the 3D registration (surface range data) yields a 3D deformation (FIG. 8 step (k)). The 2D deformations are back-projected onto 3D space to provide a combined 3D image.

FIGS. 4A and 4B demonstrate the back-projections of the 2D deformation from the top-view and side-view, respectively where FIG. 4A shows the x-ray projection for top-view and FIG. 4B shows an optical side-view photo. The same principles also apply if the optical photo is taken from the top-view and the x-ray is projected from the side-view where p is an arbitrary vertex of the atlas mesh, p' is the projection point of p onto the detector (either x-ray detector or camera detector), and s is the x-ray point source or camera aperture. The 2D deformation is characterized by a 2D coordinate system (m, n) which is set on the detector. The 2D deformation vector of p' is defined as $v(p')=[v_m(p'), v_n(p')]$. For the top-view projection, $v^T(p)=[v_x^T(p), v_y^T(p), v_z^T(p)]$ was used to denote the 3D deformation vector. $v^T(p)$ is back-projected from $v(p')$ using $$v_x^T(p) = \frac{|sp|}{|sp'|} v_m(p') \qquad (7)$$
$$v_y^T(p) = \frac{|sp|}{|sp'|} v_n(p')$$
$$v_z^T(p) = 0,$$

where $|sp|$ and $|sp'|$ are the distances from s to p and p', respectively. For the side-view projection, $v^S(p)=[v_x^S(p), v_y^S(p), v_z^S(p)]$ was used to denote the 3D deformation vector where $v^S(p)$ is back-projected from the $v(p')$ using $$v_x^S(p) = 0 \qquad (8)$$
$$v_y^S(p) = \frac{|sp|}{|sp'|} v_n(p')$$
$$v_z^S(p) = \frac{|sp|}{|sp'|} v_m(p').$$

The back-projections using equations (7) and (8) preserves the collinearity of the points in the line sp' after the 3D deformation. By imposing this collinearity requirement, implausible 3D distortions of organ anatomy are avoided. However, such requirement can over-constrain the anatomical variations of inter-subject registration. This problem is addressed below.

Where the projections are taken from oblique angles (e.g. θ=45°), the principle of back-projection is similar to the procedure described above. However, a difference is that the world coordinate system is rotated clock-wise along the y-axis so that angle θ becomes the top-view, and θ+90° becomes the side-view.

After the 2D deformations are back-projected onto 3D, the deformations of different modalities are combined together. In a preferred embodiment, the 11 evaluated combinations set forth above are based on the following principles:

(1). no more than three modalities are included in the combination;

(2). if 2D modalities (x-ray imaging and optical camera) are included, there are no more than two 2D modalities; and (3) if two 2D modalities are included, they must be orthogonal to each other so that redundant projection is avoided.

Based on these principles, a three-element binary vector $b=[b^T, b^S, b^L]$ was used to describe the composition of the combination, where $b^T$, $b^S$, $b^L$ represent the presence of top-view, side-view and laser range data, respectively. $b^T=1$ indicates the inclusion of a top-view 2D image, $b^T=0$ indicates exclusion of the top-view 2D image, and so forth for $b^S$ and $b^L$. For example, the combination of "C0+C90" has the b value of [1, 1, 0], and the combination of "X0+C90+L" has the b value of [1, 1, 1]. The deformations of different modalities are combined into one 3D global deformation according to $$v_x(p) = \frac{b^T v_x^T(p) + b^L v_x^L(p)}{b^T + b^L} \qquad (9)$$
$$v_y(p) = \frac{b^T v_y^T(p) + b^S v_y^S(p) + b^L v_y^L(p)}{b^T + b^S + b^L}$$
$$v_z(p) = \frac{b^S v_z^S(p) + b^L v_z^L(p)}{b^S + b^L},$$

where $v(p)=[v_x(p), v_y(p), v_z(p)]$ is the combined deformation and $v^L(p)=[v_x^L(p), v_y^L(p), v_z^L(p)]$ is the deformation of the laser scan.

Validation of Registration Accuracy

For each of the 11 combinations listed in Table 2 and shown in FIG. 9 the 23 target subjects were imaged with the method to prepare simulations described above. As a result, 253 (i.e., 11×23) sets of images were generated. Each of the five atlases were registered with the 253 sets of images, to provide 1265 registration result (i.e., 5×253). For each registration result, the registration accuracy of each organ was measured using the Dice coefficient.

$$\text{Dice} = 2 \frac{|R_A \cap R_S|}{|R_A| + |R_S|}, \qquad (10)$$

where $R_A$ and $R_S$ represent the organ region of the registered atlas and the target subject, respectively (|•| denotes the number of voxels and ∩ represents the overlapping between two regions).

The Dice coefficient has the value range of [0, 1]. If two regions completely overlap with each other, the Dice coefficient is 1; if two regions have no overlap at all, the Dice coefficient is 0.

To evaluate the registration accuracy of different combinations for different organs, the mean Dice coefficients and standard deviations were calculated based on the 5×23=115 results of each combination. The statistics are shown in FIGS. 10A, 10B, 10C and 10D, where the 10 organs are displayed in four graphs. These results were calculated across different atlases in order to reduce the possible bias of using any individual atlas.

Figure 10A:
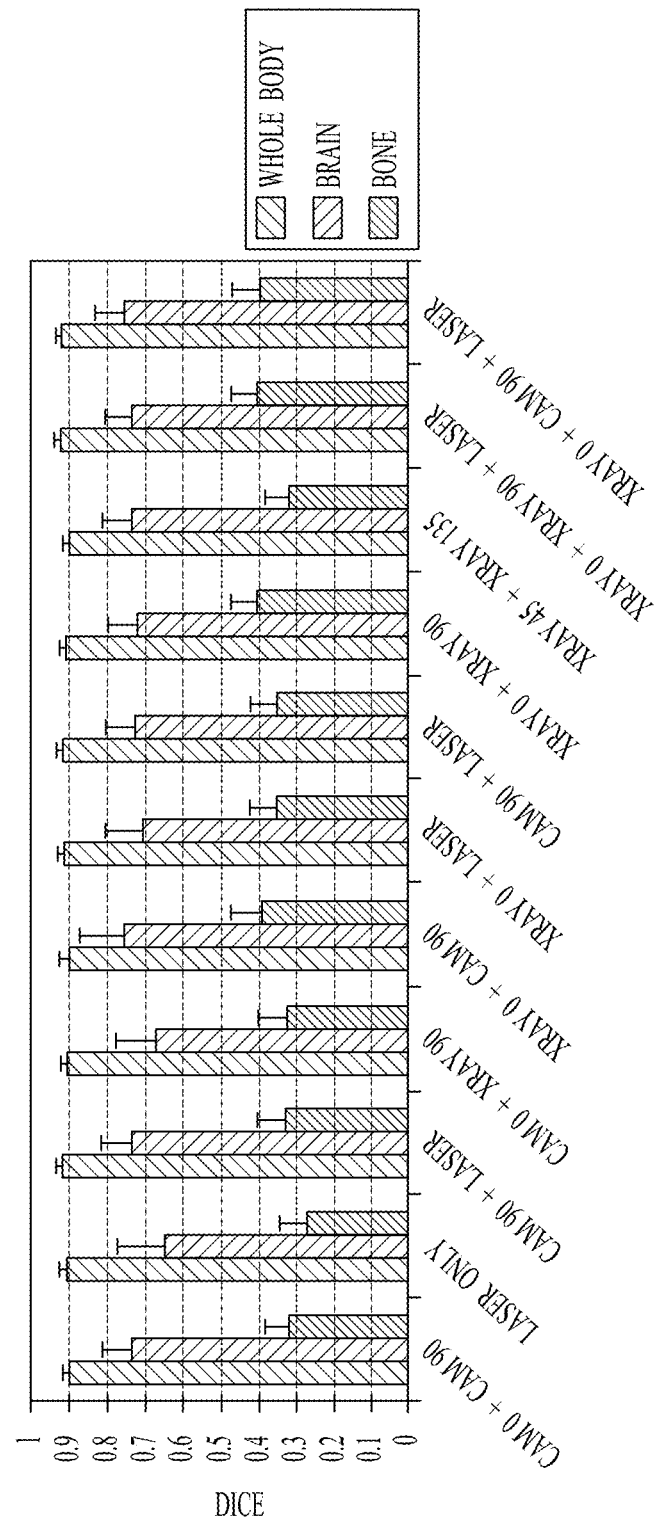
FIG. 10A-FIG. 10D comprises 4 graphs showing the registration accuracy (Dice coefficients) of different combinations of the non-tomographic modalities where
Figure 10B:
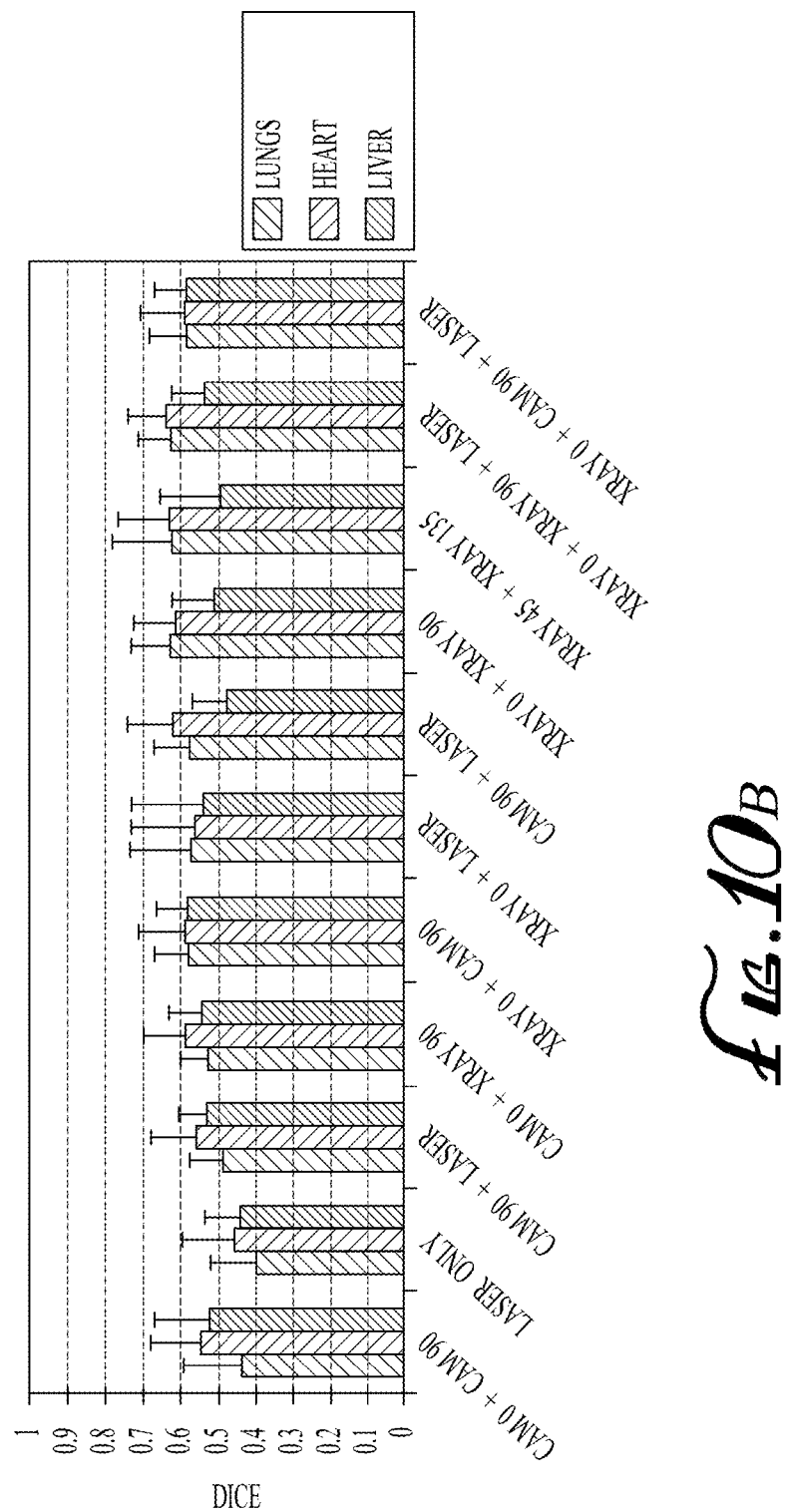
Figure 10C:
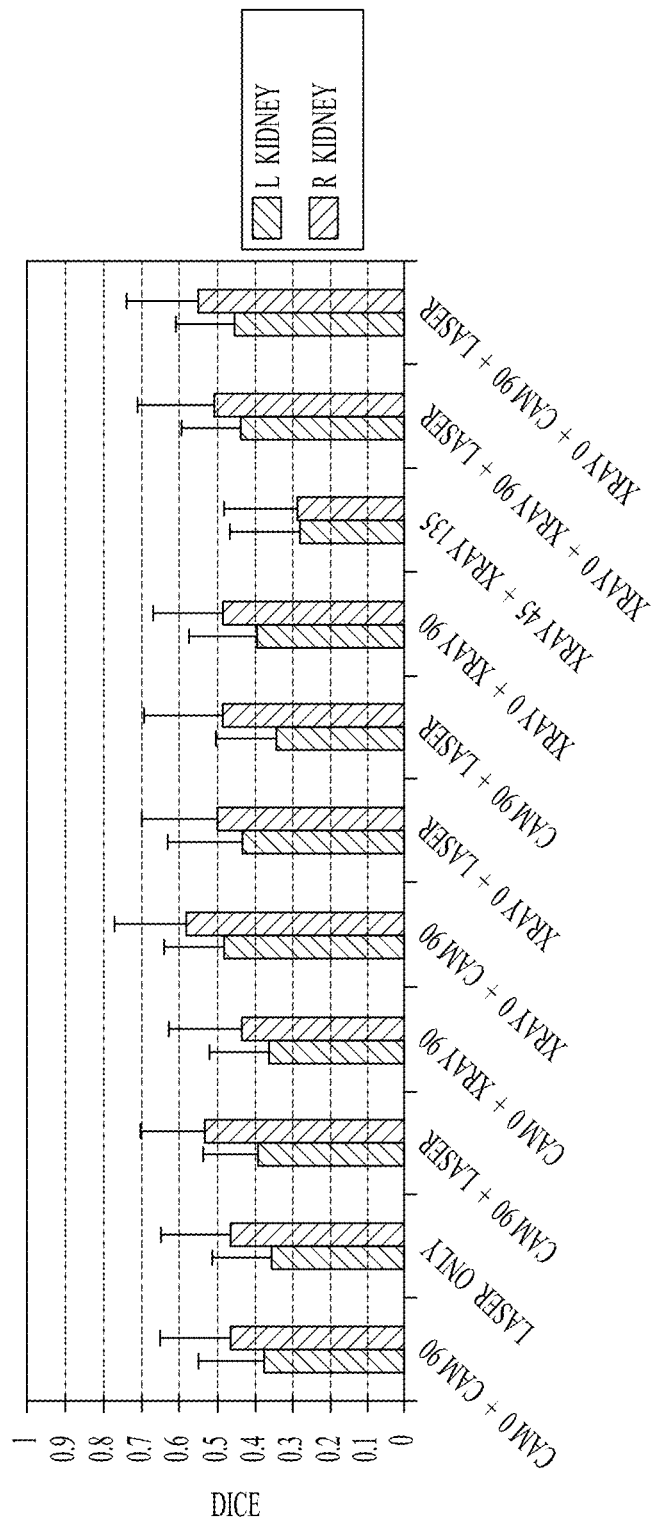
Figure 10D:
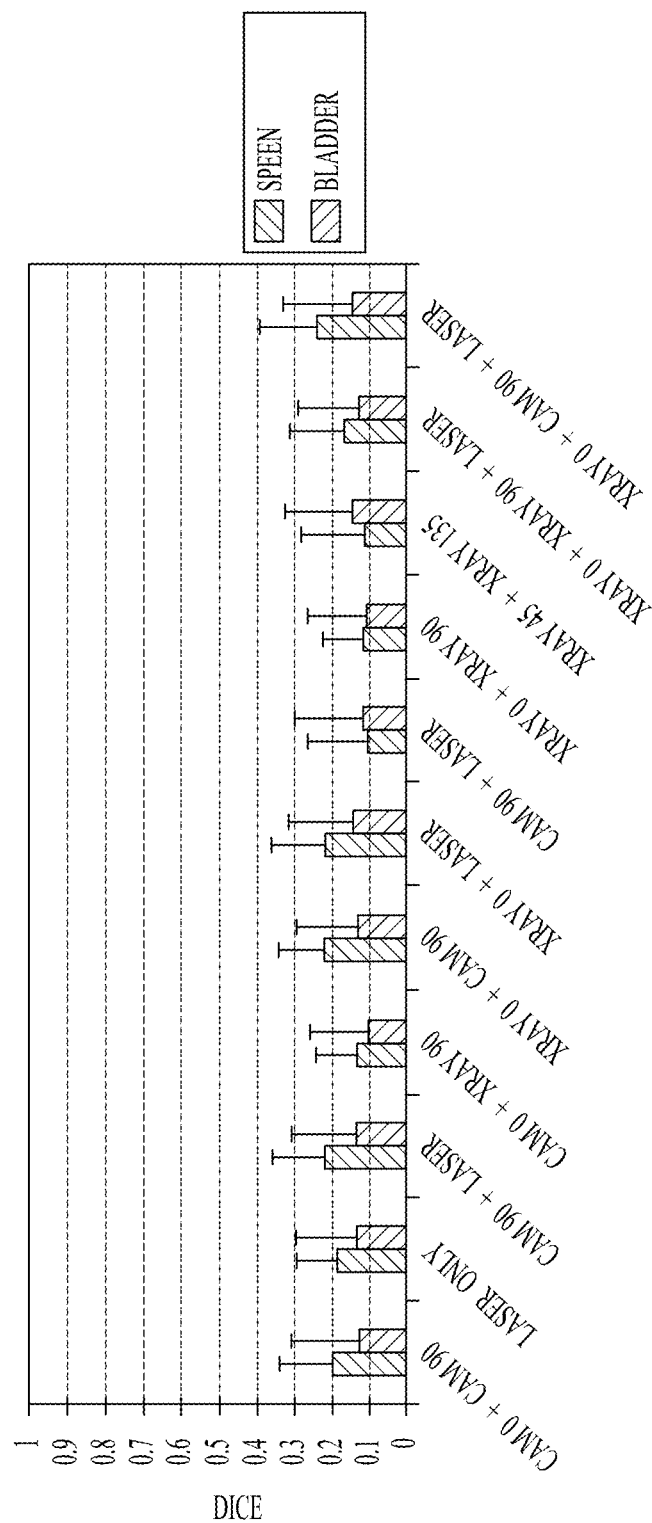
Figure 11:
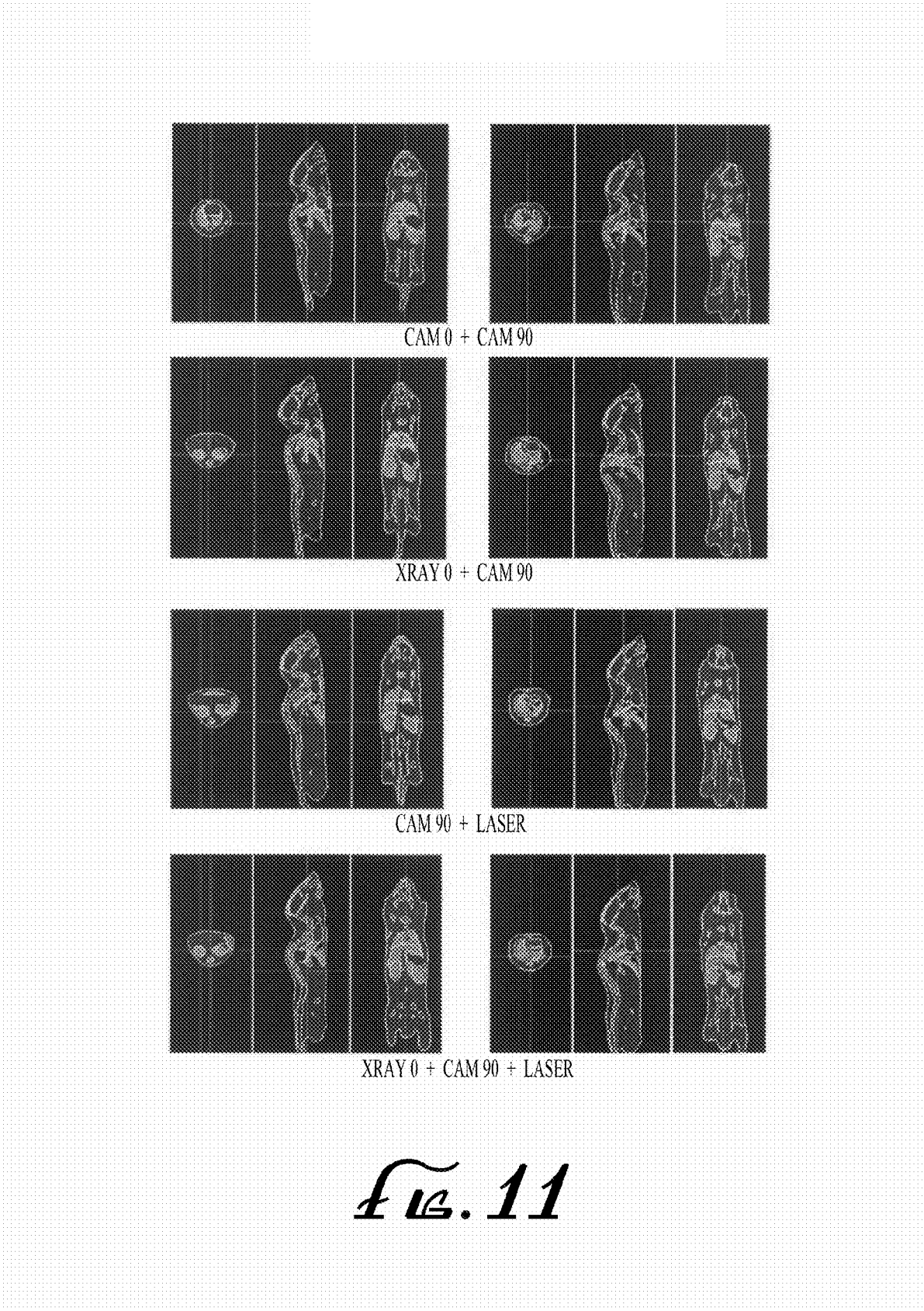
FIG. 11 is a composite showing images of representative registration results for four combinations, namely CAM0+CAM90; XRAY0+CAM90; CAM90+LASER AND XRAY0+CAM90+LASER.

As a demonstration of the registration results, representative images of the registration results for four combinations are shown in FIG. 11, i.e. "C0+C90", "C90+L", "X0+C90", and "X0+C90+L". "C0+C90" and "C90+L" are the two least expensive combinations from the basis of hardware implementation; while "X0+C90" and "X0+C90+L" provide two combinations with the best compromise between the accuracies of high x-ray contrast structures (skin, skeleton and lungs) and low x-ray contrast structures (heart, liver, spleen, kidneys and bladder), according to the results in FIGS. 10A-10D. For each combination, both good and imperfect or poorer results are demonstrated. The good examples are selected from the cases where the atlases match well with the subjects while the imperfect or poorer examples are selected from the cases where the atlases match poorly with the subjects. For the imperfect examples, the same subject is shown for the four combinations to reveal the differences between the combinations. In FIG. 11, each row shows one combination; the left column shows the good cases, and the right column shows the inaccurate cases.

The white contours indicate the registered atlases, and the various gray filled regions indicate the target organs.

The registration workflow was programmed with IDL 7.1 (ITT Visual Information Solutions, Boulder, Colo., USA). The Elastix™ toolbox was accessed online by the IDL program. The registration was executed on a PC with a 3.05 GHz CPU and 5.99 GB RAM. The time requirements were ≈20 s for the registration of each 2D image (camera photo or x-ray projection), and ≈2 min for the registration of each laser scan. The whole workflow generally took 4-6 iterations. Combinations 1-5 in Table 2 took 3-5 min, combination 6 (L only) took 8-12 min, combination 7-9 took 10-14 min, and combination 10 and 11 took 11-17 min. In summary, the combinations without surface scanning took less than about 5 minutes while including surface scanning in the process increased the time to less than about 20 minutes.

Accuracy of Different Organs

Based on FIGS. 10A-10D, it can be seen that different organs have different levels of accuracy. "Whole Body" had the largest Dice coefficient (Dice≈0.9) and the smallest standard deviation. This is because the whole body is the most obvious region in the acquired images. The brain also has high accuracy (0.6≤Dice≤0.8), because its shape and position is highly correlated to the head outline which is clear in both optical photos and X-ray projections. The bones have low accuracy (Dice≤0.4), because they have long and curved shapes which are difficult to match precisely. The lungs, heart and liver have the same level of Dice coefficient (0.4≤Dice≤0.6), because they are in the same anatomical region, i.e. the thoracic and upper abdominal region. Compared to other soft organs, the lungs, heart and liver are larger in size and more stable in position than other internal organs. Therefore they are more accurately registered than other soft organs. In regard to the kidneys, it was found that the right kidney (0.3≤Dice≤0.6) is always more accurate than the left kidney (0.3≤Dice≤0.5), because the position of the right kidney is affected by the liver (which is large and stable), while the position of the left kidney is affected by the stomach (which varies in size according to food contents). The spleen (Dice≤0.35) and the bladder (Dice≤0.15) have the smallest Dice coefficients and the largest standard deviations. It is noticeable that the standard deviation of the bladder is even larger than its mean value (see FIG. 10D, which is interpreted to mean that the accuracy distribution of the bladder is highly scattered and skewed. This is because the bladder anatomy is strongly affected by urine production which is a random process. The spleen is inaccurate because it has long and thin shape, and its position is affected by the surrounding big organs, such as the highly variable stomach. Even a slight mismatch of the spleen position or direction will cause a significant decrease of the corresponding Dice coefficient.

Influence of the Combination of Non-Tomographic Modalities

FIGS. 10A-10D reveal the influence of different non-tomographic imaging modality combinations on registration accuracy. For example, adding X-ray projections improves the accuracy of the bones, lungs and heart; adding a laser scan improves the accuracy of the spleen and kidneys. By analyzing the three all optical combinations, C0+C90, L Only and C90+L., based on a comparison of L Only with C0+C90, it appears that L Only is less accurate than C0+C90 in terms of most soft organs. However, L Only provides richer stereo information than C0+C90. This is because L Only overemphasizes surface alignment, thereby sacrificing the accuracy of internal organs. Comparing the all-optical combinations with the combinations that contain x-rays, a main difference is that the combinations with x-rays are more accurate for the bones, lungs and heart, because the bones and lungs have good x-ray contrast, and the heart is highly correlated with the lungs.

Significant differences can also be found on comparing the eight combinations that contain x-rays. For example, C0+X90 and X0+C90 are both composed of one X-ray projector and one optical camera. However, X0+C90 appears to be much more accurate than C0+X90. This is believed to be because the top-view x-ray can indicate the transverse curvature of the spine, while the top-view camera cannot. However, the side-view x-ray can reveal lateral curvature of the spine and this lateral curvature can also be reflected from the side-view optical silhouette. Therefore, X0+C90 would appear to be better at estimating 3D spine curvature than C0+X90. The top-view x-ray also gives a better view of the positions and shapes of the lungs and the heart, because these organs have greater anatomical variations in the transverse direction than in the lateral direction. Further, because the positions of some abdominal organs (e.g. liver, the kidneys and the spleen) are correlated with the lungs and the spine, X0+C90 also give better predictions of these abdominal organs.

From a comparison of X0+C90 with X0+X90 it appears that X0+X90 is slightly more accurate for the bones, lungs and heart because X0+X90 contains more x-ray information. However, X0+X90 is less accurate for the low x-ray contrast organs (mainly abdominal organs), because it overemphasizes the correspondence with the high x-ray contrast organs, thus sacrificing the low x-ray contrast organ registration accuracy.

X0+X90 and X45+X135 are both all-x-ray modalities. Although both of them are composed of orthogonal projections, X45+X135 has a much lower Dice coefficients than X0+X90. This result confirms the advantages of top-view and side-view over oblique views.

Comparing the combinations with and without laser scan, it can be seen that adding the laser scan only slightly increases the Dice coefficient of the whole body. This is because the Dice coefficient is mainly affected by overlapping global volume, and it is not sensitive to the improvements of local skin alignment. Based on the observations of FIG. 11 (right column), it is clear that using a laser scan improves the accuracy of local skin alignment, but this is not apparently reflected by the Dice coefficient. Nevertheless, when kidneys and spleen are concerned, adding the laser scan improves the correlation because it yields an increase of Dice coefficients as a result of the positions of the kidneys and spleen correlating well with the surface geometry.

FIG. 11 further illustrates both good and imperfect examples of the registration results, based on the C0+C90, X0+C90, C90+L and X0+C90+L combinations. The good examples shown in the left column of FIG. 11 are mainly selected from the subjects that are similar to the atlas in body size, shape and internal organ distributions. However, even for these good examples, a perfect match of the bladder is not guaranteed. From the imperfect examples in the right column of FIG. 11, important informative differences between the combinations can be seen. C0+C90 has poor alignment of the internal organs because the optical photos contain no internal anatomy. The accuracy of internal organs is much improved in X0+C90 which has much better accuracy (especially for skeleton and lungs) because of the use of x-rays. Because C0+C90 and X0+C90 rely only on 2D modalities, they both have imperfect matches with the skin. By using the laser scanner, C90+L and X0+C90+L achieve much better alignment of the skin. This is important to those applications which require good skin registration, such as optical tomographic reconstruction. Comparing C90+L with X0+C90+L, X0+C90+L has better accuracy of the internal organs, due to the use of x-rays.

Influence of Different Atlases

To evaluate the influence of using different atlases, five mouse atlases generated from 5 different mice were registered to 23 target subjects. From FIG. 6, significant inter-atlas differences of internal organs can be observed. Atlas 1 and 2 are generally more accurate than the other three, because atlas 1 and 2 represent regular anatomy (in terms of overall body size and shape, as well as internal organ shapes and positions) of the majority subject population. As for atlas 3, 4 and 5, it is hard to tell which one is best, because they outperform each other on different organs and different combinations. The conclusion from these findings is the importance of selecting an atlas that represents the majority of the target population, in order to conduct statistically accurate registrations. Such selection may require prior knowledge of the population's anatomical type, such as age, weight, strain, sex, etc.

Comparison with Previous Studies

As discussed above, several previous studies on mouse atlas registration with certain non-tomographic modalities have been reported. A difference between the presently disclosed procedure and previous work is the scope of the modalities used. The embodiments disclosed herein includes 11 different combinations of three non-tomographic modalities, while the previous studies mainly included one optical modality, i.e. optical cameras or surface scanners. While the presently described process does include two combinations that are the same as previous studies (C0+C90 and L Only), it is difficult to directly compare the present procedure with the prior reported approaches in terms of registration accuracy, because the previous studies were based only one or two test subjects. Nevertheless, as shown in prior studies. whole body and brain tend to have larger Dice coefficients than internal organs, and skeleton, spleen and bladder tend to have the lowest Dice coefficients. As shown in FIG. 10B, C0+C90 and L Only were also found to be the least accurate of the 11 combinations for simulating lung, heart and liver locations and size.

Besides registration with non-tomographic modalities, there also exists previous work on registration with fully tomographic imaging modalities such as micro-CT and micro-MR. A comparison of the results obtained with the present procedures with the accuracy with these prior reported methodologies shows that the Dice coefficients of the procedure reported herein, taking into consideration all the 11 combinations, are generally lower than those from fully tomographic registrations. However, the use of non-tomographic registration as reported herein results in a reduction in methodology and implementation costs, as well as a reduction in time to obtain useful simulations, in exchange for a slight reduction in registration accuracy. It is recognized that the expected reduction in registration accuracy is not detrimental in certain applications or procedures. Further, an advantage of the non-tomographic systems and embodiments described herein over a fully tomographic system is that the non-tomographic system is easier to be combined with molecular imaging systems (e.g. PET, SPECT and optical tomography). Normally, if one wants to co-register a fully tomographic modality with a molecular imaging modality, the two systems should either be physically combine or one must rely on the transfer of a specially designed sample (mouse) holding chamber that can be moved from one system to the other. The limitations of these two alternative solutions are that the first one suffers from the complexity of the fully tomographic system, and the second one has the inherent risk of animal movements. Considering these limitations, incorporating a simpler non-tomographic system as described herein with the molecular imaging modalities appears to provide a unique and cost effective alternative to prior techniques.

An advantage of the procedures set forth herein is the registration method design. This method enables atlas registration with flexible combinations of the non-tomographic modalities. The algorithm is implemented based on the publicly accessible Elastix™ registration toolbox. The computation cost using a standard PC is reasonable and is fully automatic. These benefits make this method easy to implemented and use. Compared with most prior 2D/3D registration methods, which jointly register the atlas with 2D projections via direct 3D deformation, this method separately registers the atlas with each 2D projection and back-projects the 2D deformations into 3D under a collinearity constraint. The reason that joint registration is not the preferred route is that direct 3D deformation has many more degrees-of-freedom than does 2D deformations. As a result, 3D shape constraints (such as statistical shape modeling) are needed to regularize the 3D deformation. Building a statistical shape model of the whole-body mouse anatomy is complicated due to the involvement of multiple subjects and multiple organs. Collinearity constraints provide a simpler method to regularize the atlas deformation. Based on the results set forth above, this constraint works well with the 11 imaging combinations. However, the collinearity constraint tends to over-constrain the inter-subject deformation.

Another unique feature of the procedure described herein is the use of self-made atlases. Contrast-enhanced CT images were used to generate different atlases, and it was found that the best atlas is the one that represents the majority of the subject population. This result suggests that subject-specific atlases produced for the test population and the intended application is the preferred option.

Accordingly, as part of the procedure set forth above, the registration of a multi-subject statistical mouse atlas to non-contrast micro-CT images, for the purpose of estimating gross anatomy of major organs, was prepared. Focus was on the trunk region which includes most of the important organs for pre-clinical bio-distribution studies. The statistical mouse atlas was constructed based on 45 subjects used to achieve better ability of compensating inter-subject anatomical variations than a single atlas. The statistical shape model (SSM) (T. Heimann and H. P. Meinzer, "Statistical Shape Models For 3D Medical Image Segmentation: A Review," Med. Image Anal., vol. 13, pp. 543-563, (August 2009)) was used to learn the inter-subject anatomical variations. A conditional Gaussian model (CGM) was then used to capture inter-organ correlations of shapes and positions. For atlas registration, the statistical shape model was used to align the high-contrast organs, and the conditional Gaussian Model was used to estimate low-contrast organs from high-contrast organs. Described below is the construction and registration of the statistical atlas and the evaluation results of registration accuracy.

Method of Atlas Construction.

Figure 12:
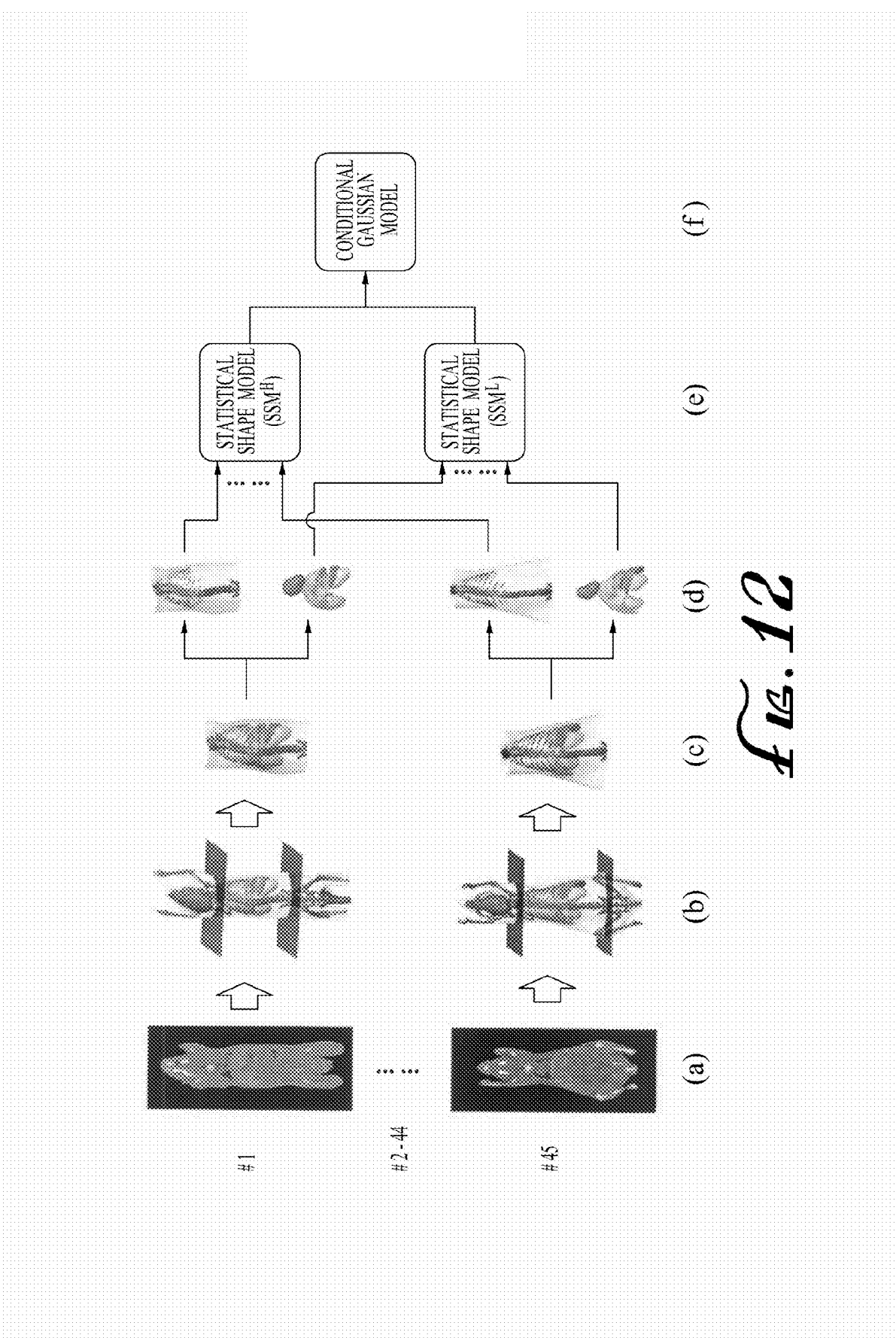
FIG. 12 is a schematic drawing showing construction of the statistical mouse atlas of the mouse trunk region comprising steps a-g where (a) is compiled from a set of 45 contrast-enhanced micro-CT images; (b) illustrates two axial slices passing through the neck and pelvis; (c) shows the trunk region cut out between the two axial slices; (d) shows the segmented organs divided into two groups comprising high-contrast organs and low-contrast organs; (e) shows the step of two statistical shape models being constructed for the high-contrast organs and low-contrast organs, respectively and (g) represents a conditional Gaussian model constructed based on the two statistical shape models.

A schematic representation of the procedure for construction of a statistical mouse atlas of the mouse trunk region is shown in FIG. 12. FIG. 12 step (a) represents a composite of a set of 45 contrast-enhanced micro-CT images. Segmented organs are shown by various gray image contours. The two axial slices that pass the neck and pelvis are made, as shown in FIG. 12 step (b). The trunk region is then cut out between the two axial slices (FIG. 12 step c). In step (d) segmented organs are divided into two groups: comprising high-contrast organs and low-contrast organs. Two statistical shape models are then constructed for the high-contrast organs and low-contrast organs, respectively (FIG. 12 step (e)) and a conditional Gaussian model is constructed based on the two statistical shape models (FIG. 12 step (g)). These steps are further described below.

1). Mouse Subjects:

As shown in FIG. 12 step (a), 45 contrast-enhanced mouse micro-CT images obtained from normal subjects were used for atlas construction. These images were selected from previously acquired datasets of contrast agent studies. Healthy subjects of different sexes, strains, weights and postures were acquired in vivo. Three of the most frequently used mouse strains used in preclinical studies (Nude, black C57, and severe-combined immunodeficient (SCID)) were included, with body weights ranging from 15 g to 30 g. The subjects were imaged at prone positions inside a multimodality chamber, such as shown in FIGS. 23 and 24, that provided anesthesia and heating. Although the imaging chamber restrained the possible postures of the mouse subject, these were not strictly regularized and random flexing of bodies towards the left, right and back directions was included in the dataset. The contrast agent used was Fenestra™ LC (ART, Quebec, Canada) and the imaging system was a MicroCAT II small animal CT (Siemens Preclinical Solutions, Knoxville, Tenn., USA). Exposure settings were 70 kVp, 500 mAs, 500 ms and 360° rotation in 10 steps with 2.0 mm aluminum filtration. Images were reconstructed using a modified Feldkamp process to isotropic voxel size 0.20 mm, and a matrix size 256×256×496.

The major organs that were visible in the contrast-enhanced CT images were segmented using a semi-automatic segmentation software, which incorporated intensity thresholding, region growing, deformable simplex mesh and graph cut tools. The segmented organs included skin, skeleton, heart, lungs, liver, spleen and kidneys. All the segmented organs were converted to triangular surface meshes using the Marching Cubes Algorithm (E. L. William and E. C. Harvey, "Marching Cubes: A High Resolution 3D Surface Construction Algorithm," in *Proc. Computer Graphics and Interactive Techniques (SIGGRAPH* 87), pp. 163-169 (1987)). To reduce the computational cost for the subsequent registration step, the triangular meshes were reduced to fewer vertex numbers: 2500 for skin, 2000 for skeleton, 1000 each for lungs and liver, 700 each for the heart, spleen and kidney. These numbers were selected as tradeoffs between reducing computation cost and maintaining organ shape features. To extract the trunk region, two axial slices were manually selected passing through the neck bone and the pelvis bone, respectively (FIG. 12 step (b)). This extracted region between the two axial slices covers the areas of biological interest, including all the major organs other than brain (FIG. 12 step (e)). To establish the vertex correspondence between different subjects, a reference subject of each organ was selected and registered to the rest of the subjects (i.e. the correspondence of each organ was established separately) using the point set registration method based on Gaussian mixture models.

2). Statistical Shape Model.

The statistical shape model (SSM) has been widely used for modeling anatomical variations of biological structures (F. L. Bookstein, "Shape And The Information In Medical Images: A Decade Of The Morphometric Synthesis," *Comput. Vision Image Understanding*, vol. 66, pp. 97-118, (1997)), incorporated herein in its entirety by reference, and has been successfully used for registration and segmentation of human organs. SSM was also used to model the inter-subject anatomical variance of the major mouse trunk organs.

According to their visibility in non-contrast enhanced micro-CT images, the segmented organs were divided into two groups: high-contrast organs (skin, skeleton and lungs) and low-contrast organs (heart, liver, spleen and kidneys) (FIG. 12 step (d)) and two statistical shape models, $SSM^H$ and $SSM^L$, were constructed for each group, respectively (FIG. 12 step (e)).

Before the construction of the $SSM^H$, the inter-subject differences of translation, scaling and rotation were eliminated using the Generalized Procrustes Analysis (F. L. Bookstein, "Landmark Methods For Forms Without Landmarks: Localizing Group Differences In Outline Shape", *Proc. Mathematical Methods in Biomedical Image Analysis (MMBIA* 19, *Journal of Educational Psychology*, pp. 279-289 (1996)) where $M_i^H$ denotes the mesh of high-contrast organs of the $i^{th}$ subject index. The Generalized Procrustes Analysis was applied to the set of $\{M_i^H|i=1, 2, \ldots, 45\}$ to obtain the similarity transformations $\{SIM_i^H|i=1, 2, \ldots, 45\}$ that mapped each $M_i^H$ into the generalized shape space. When $m_i^H = SIM_i^H(M_i^H)$ denotes the mesh after the Procrustes alignment, $m_i^H$ is represented as a 1D vector which is lined up with the 3D coordinates of the mesh vertices, $$m_i^H = \{x_i^{skin}, x_i^{skeleton}, x_i^{lungs}\}, \tag{11}$$

where $x_i^{skin} = \{x_{i,1}^{skin}, y_{i,1}^{skin}, z_{i,1}^{skin}, x_{i,2}^{skin}, y_{i,2}^{skin}, z_{i,2}^{skin}, \ldots, x_{i,N^{skin}}^{skin}, y_{i,N^{skin}}^{skin}, z_{i,N^{skin}}^{skin}\}$, with $(x_{i,j}^{skin}, x_{i,j}^{skin}, x_{i,j}^{skin})$ being the 3D coordinates of the $j^{th}$ vertex of subject i, and $N^{skin}$ being the total number of skin vertices. The same notations also apply to skeleton and lungs. Therefore $m_i^H$ is a 1D vector of length $3 \times (N^{skin} + N^{skeleton} + N^{lungs})$.

Principal component analysis (PCA) (H. Hotelling, "Analysis Of A Complex Of Statistical Variables Into Principal Components," *J. Educ. Psychol.*, vol. 24, pp. 498-520, (1933)) was performed based on the set of $\{m_i^H|i=1, 2, \ldots, 45\}$. This statistical analysis technique reduces data dimensionality of multivariate datasets. It linearly transforms the datasets into a new coordinate system where the first coordinate corresponds to the direction of greatest variance of data distribution, the second coordinate corresponds to the direction of second greatest variance, and so on. The directions of the new coordinate basis were defined as the eigenvectors of the covariance matrix of the datasets, with the eigenvalues as the energy of data variance in the corresponding directions. Each eigenvector was considered as a principal component of the original dataset. Using PCA, it is possible to simplify the representation of the datasets as a linear combination of the first few principal components. In the present procedure, the principal components corresponded to the statistical variations of $\{_i^H|i=1, 2, \ldots, 45\}$. By performing eigendecomposition to the covariance matrix of $\{m_i^H|i=1, 2, \ldots, 45\}$, the eigenvalues $\lambda_m^H$ and eigenvectors $v_m^H$ (m=1, \ldots, M) were obtained. The first $\hat{m}$ components that account for over 95% of the total variations (i.e. $\sum_{m=1}^{\hat{m}} \lambda_m^H \geq 0.95 \sum_{m=1}^{M} \lambda_m^H$) were grouped columnwisely into a matrix $V^H$ which satisfied $(V^H)^T V^H = I$. The $SSM^H$ is represented as $$m^H = \overline{m}^H + V^H b^H \tag{12}$$

where $m^H$ is an arbitrary instance of the model, $\overline{m}^H$ is the mean value of $\{m_i^H\}$, and $b^H$ is a $\hat{m}$ component 1D vector of the shape parameters. The shape parameters of each $m_i^H$ were computed as $$b_i^H = (V^H)^T (m_i^H - \overline{m}^H) \tag{13}$$

The construction of $SSM^L$ was the same as for $SSM^H$, except for the Procrustes alignment step. In order to map $\{M_i^H\}$ and $\{M_i^L\}$ into the same shape space, $\{M_i^L\}$ was normalized using the similarity transformations of $\{M_i^H\}$, i.e. $m_i^L = SIM_i^H(M_i^L)$. Therefore $SSM^L$ was represented as $$m^L = \overline{m}^L + V^L b^L \qquad (14)$$

and the shape parameters for each $m_i^L$ were computed as $$b_i^L = (V^L)^T(m^L - \overline{m}^L) \qquad (15)$$

3). Conditional Gaussian Model:

The conditional Gaussian model (CGM) is a mathematical tool for modeling the conditional distribution between two multivariate Gaussian variables. CGM has been used to describe the correlations between sparse vertebrae landmarks and dense vertebrae edge points of human lateral X-ray spine images. In the present procedure, the conditional Gaussian model was used to capture the shape correlation between $SSM^H$ and $SSM^L$ (FIG. 12 step (f)). Given that $SSM^H$ was matched to the micro-CT image, the conditional Gaussian model was used to estimate the conditional distribution of $SSM^L$. The basic assumptions were that the probabilistic distribution of $SSM^H$ and $SSM^L$ could be modeled with Gaussian distributions, and there exist statistical correlations between $SSM^H$ and $SSM^L$. The feasibility of these assumptions is verified in the appendix section, where we plotted the distributions of $b^H$ and $b^L$, as well as the covariance matrix between different organs. Observations based on these plots confirmed that $b^H$ and $b^L$ roughly follow Gaussian distributions, and there were apparent correlations between different organs. While the possible existence of better distribution models for describing the inter-organ correlations is not denied, the conditional Gaussian model works reasonably well in this application.

The construction of the conditional Gaussian model is as follows. Based on the subjects, the probabilistic distributions of $b^H$ and $b^L$ were modeled with multivariate Gaussian distributions, and the conditional distributions between $b^H$ and $b^L$ were modeled with a conditional Gaussian distribution, $$P(b^L | b^H) = N(\overline{b}^{L|H}, \Sigma^{L|H}) \; \overline{b}^{L|H} = \overline{b}^L + \Sigma^{L,H}(\Sigma^H)^{-1}(b^H - \overline{b}^H)$$
$$\Sigma^{L|H} = \Sigma^L + \Sigma^{L,H}(\Sigma^H)^{-1}\Sigma^{H,L} \qquad (16)$$

where $\overline{b}^{L|H}$ and $\Sigma^{L|H}$ are the mean and covariance of the conditional distribution; $\underline{b}^H, \Sigma^H$ and $\overline{b}^L, \Sigma^L$ are the mean and covariance of $b^H$ and $b^L$, respectively; $\Sigma^{L,H}$ and $\Sigma^{H,L}$ are the cross-covariance between $b^H$ and $b^L$, respectively. The values of $\overline{b}^H, \Sigma^H, \overline{b}^L, \Sigma^{L,H}$ and $\Sigma^{H,L}$ can be estimated from the set $\{b_i^H | i=1, 2, \ldots, 45\}$ and $\{b_i^L | i=1, 2, \ldots, 45\}$.

Figure 13:
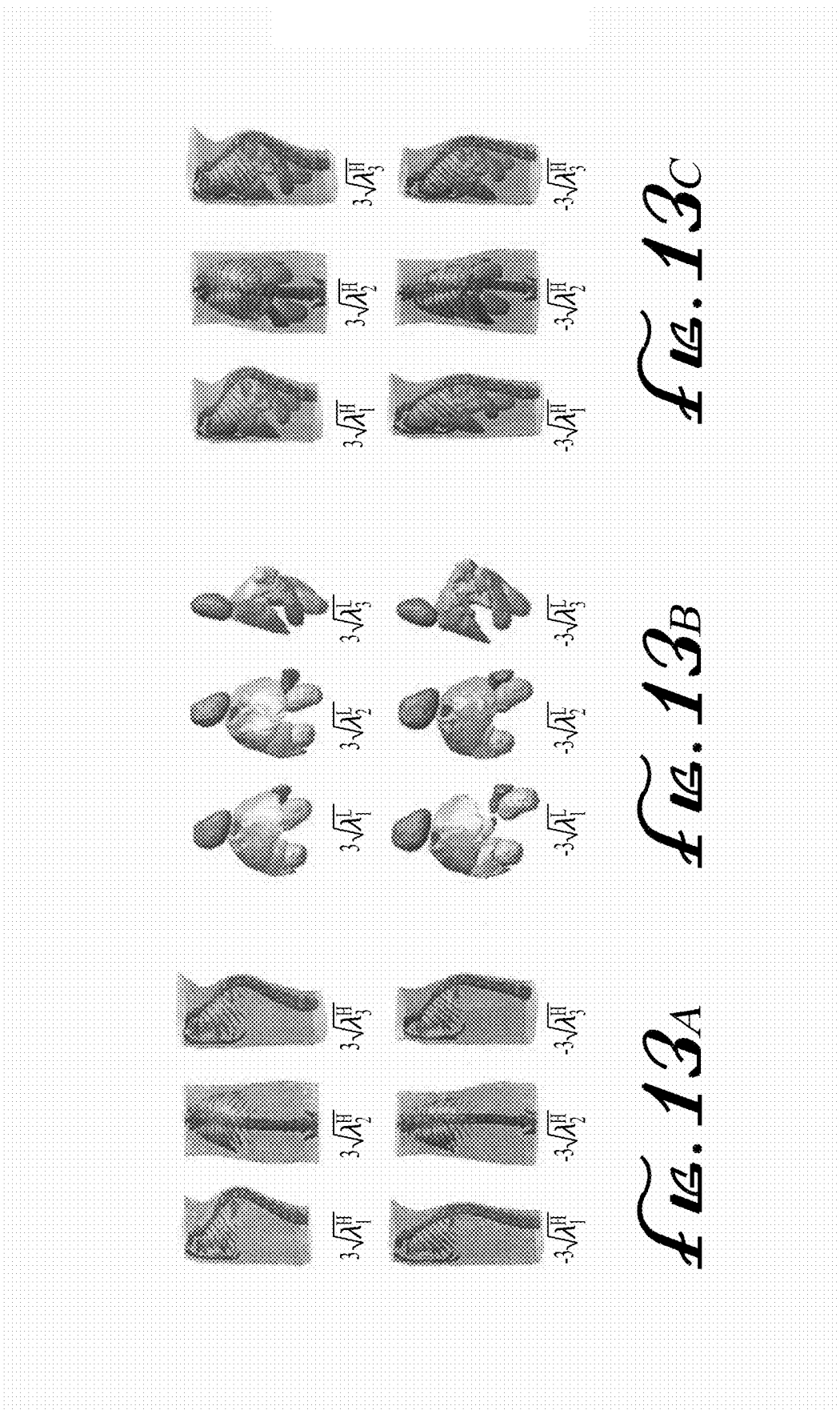
FIG. 13C shows the eigenmode combinations of $SSM^H$ and the $SSM^L$ shape variations.

FIGS. 13A, 13B, and 13C illustrate the shape variations generated from the statistical shape models and the conditional Gaussian model. FIG. 13A shows the shape variations of the first three principle modes of $SSM^H$. The left column shows the variation of the largest eigenmode between $3\sqrt{\lambda_i^H}$ (top) and $-3\sqrt{\lambda_i^H}$, the middle and right columns show the variations of the second and third largest eigenmode, respectively. FIG. 13B shows the shape variations of $SSM^L$ in the same manner. FIG. 13C shows the shape correlations generated from the conditional Gaussian model: when both $SSM^H$ and $SSM^L$ are displayed together, the shapes of $SSM^H$ are the same as FIG. 13A, and the corresponding shapes of $SSM^L$ are generated using the conditional Gaussian model, based on the shapes of $SSM^H$ as the conditions. It can be observed from FIG. 13C that the shape variations of $SSM^L$ closely follow the shape variations of $SSM^H$.

B. Atlas Registration

Figure 14:
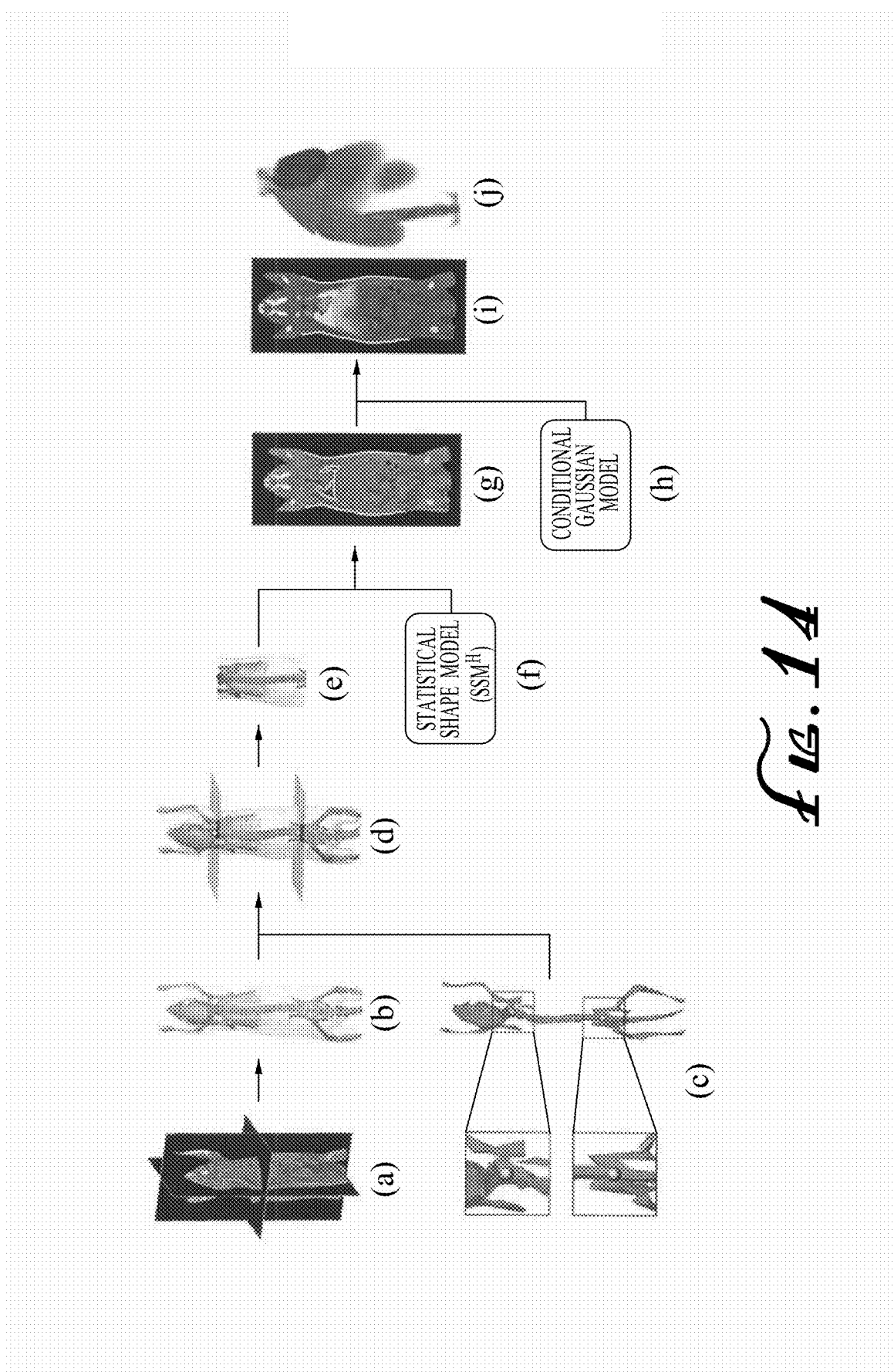
FIG. 14 illustrates the sequence for atlas registration with steps a-j where (a) is a target micro-CT image, (b) shows high contrast organs segmented from the CT image, (c) illustrates a single-subject skeleton atlas used for trunk segmentation with the enlarged images to the left showing the two landmark points that are used for marking the trunk range, (d) shows the skeleton atlas registered with the segmented organs and two axial slices passing through the landmarks (e) shows the trunk region of the segmented meshes cut out by the two axial slices of (d), (f) represents a statistical shape model of high contrast organs ($SSM^H$) and (g) shows the results of fitting $SSM^H$ to the target subject.

The registration of the statistical atlas is achieved in three steps: segmentation of high-contrast organs, registration of high-contrast organs, and estimation of low-contrast organs. FIG. 14 illustrates the process of atlas registration, which is explained below.

FIG. 14 step (a) shows a target micro-CT image formation. High contrast organs are segmented from the CT image (step (b)). A single-subject skeleton atlas as shown in step (c). is used for trunk segmentation. The enlarged regions shown in the left portion of step (c) illustrate the two landmark points that are used for marking the trunk range. The skeleton atlas is registered with the segmented organs (step (d)) and two axial slices are generated passing through the registered landmarks. In FIG. 14 step (e) the trunk region of the segmented meshes, which is cut out by the two axial slices of step (d) is shown. A statistical shape model of high contrast organs ($SSM^H$) (step (f)) is applied to generate step (g) which is the result of fitting $SSM^H$ to the target subject. A Conditional Gaussian model (step (h)) is used to generate probability maps of the registered organs (step (i)) overlaid with the target CT image (step (j)).

1) Segmentation of High-Contrast Organs:

To obtain the alignment features for atlas registration, high-contrast organs were segmented from the micro-CT image (FIG. 14 steps (a) and (b)). The ISODATA clustering method ("Thresholding Using The ISODATA Clustering Algorithm," IEEE Trans. *Syst. Man Cybern.*, vol. 10, pp. 771-774, (1980)) was used to group the voxels into clusters of different intensity levels. A cluster number of 8 was chosen to ensure good discrimination between the target organs. The resultant clusters were labeled from 1 to 8 based on the intensity level. Cluster 1 was classified as the background and was removed from the image, identifying the body region. Inside the body region, the cluster of the largest number of voxels (usually cluster 3 or 4) was recognized as soft tissue. Clusters brighter than soft tissue were classified as skeleton. Some subjects may have had intestine regions as bright as the bones, in part due to bits of metal in the food. These intestine regions were recognized as small disconnected objects in the lower body region and were removed from the skeleton. The lungs were classified from the upper body region as large objects which were darker than the soft-tissue and brighter than cluster 2. Finally, the Marching Cubes Algorithm was used to create the triangular mesh of the skin, skeleton and lungs.

The trunk region of the target subject was extracted by registering a single-subject skeleton atlas to the target skeleton. To reduce registration time, the mesh of the skeleton atlas was down-sampled to 400 vertices (FIG. 14 step (c)). Two landmark points were defined on the neck and pelvis of the skeleton atlas, as shown in the enlarged images of FIG. 14 step (c). The skeleton atlas was registered to the target skeleton using the point set registration method based on Gaussian mixture models (J. Bing and B. C. Vemuri, "A Robust Algorithm For Point Set Registration Using Mixture Of Gaussians," *Proc. IEEE International Conference on Computer Vision (ICCV)*, pp. 1246-1251) (2005). A TPS-based transformation was obtained from the registration and was used to map the two landmarks into the target subject. Two axial slices passing the mapped landmarks were generated (step (d)), and the trunk region was cut out between the two axial slices (step (e)).

2) Registration of High-Contrast Organs:

In the next step, $SSM^H$ (FIG. 14 step (f)) was registered to the segmented organs (step (g)). The initial correspondence between $SSM^H$ and the segmented organs was established by matching the mean shape $\overline{m}^H$ to the segmented organs using the Robust Point Matching (RPM) method (H. L. Chui and A. Rangarajan, "A New Point Matching Algorithm For Non-Rigid Registration," *Comput. Vision Image Understanding*, vol. 89, pp. 114-141, (February-March 2003)). A minor adaption was made to the RPM method in order to register multiple organs simultaneously, i.e. the point correspondences between the source and target meshes were calculated only for the vertices belonging to the same organ. The RPM method resulted in a TPS-based transformation $TPS_{init}(\bullet)$. This transformation was applied to $\overline{m}^H$ to obtain $TPS_{init}(\overline{m}^H)$, which was the initial matching result. Based on the initial matching, $SSM^H$ was registered to the segmented organs via an iterative process as follows:

1 FOR each iteration k=0, 1, 2, . . . , +∞, DO
2: IF k=0, THEN set $b^k=0$, $m^k=\overline{m}^H$, $y^k=TPS_{init}(\overline{m}^H)$
   where $b^k$ is the shape parameter at iteration k, $m^k$ is the model shape corresponding to $b^k$, and $y^k$ is the target shape of model fitting.
3: Using the Generalized Procrustes Analysis to compute the similarity transformation SIM(•) that minimizes the summed squared distance $\|y^k - SIM(m^k)\|$.
4: Calculate $b^{k+1}$ with equation (3): $b^{k+1} = (V^H)^T(SIM^{-1}(y^k) - \overline{m}^H)$.
5: Calculate $m^{k+1}$ with equation (2): $m^{k+1} = \overline{m}^H + V^H b^{k+1}$.
6: IF $\|SIM(m^{k+1}) - SIM(m^k)\| < \xi$, THEN terminate the iteration and break out.
   The termination threshold was set as g=R·N, where R was the voxel size of the CT image, and N was the total number of vertices of $SSM^H$.
7. IF $\|SIM(m^{k+1}) - SIM(m^k)\| \geq \xi$, THEN map $m^{k+1}$ into the target subject via SIM(•). For each organ mesh of $SIM(min^k)$, a ray tracing is performed along the normal directions of the vertices, to find the nearest intersecting points of the rays with the surface of the same organ in the segmentation result. These intersection points compose the new target shape $y^{k+1}$. If no intersection point is found for a specific vertex, the vertex itself is used as the intersection point.
8: The final value of $b^{k+1}$ is used as the optimal shape parameter $\hat{b}^H$. The final value of SIM(•) is used as the optimal similarity transform $\widehat{SIM}(\bullet)$. The model matching result is $\hat{M}^H = \widehat{SIM}(\overline{m}^H + V^H \hat{b}^H)$.
9: The RPM method is applied again to register $\hat{M}^H$ with the segmented organs. Let $TPS_{final}(\bullet)$ be the transformation obtained from the RPM method, the final registration result of the high-contrast organs is $$M_{Reg}^H = TPS_{final}(\widehat{SIM}(\overline{m}^H + V^H \hat{b}^H)) \quad (17)$$

The above method uses a strategy similar to the active shape model (ASM) approach (T. Heimann and H. P. Meinzer, "Statistical Shape Models For 3D Medical Image Segmentation: A Review" *Med. Image Anal.*, vol. 13, pp. 543-563, (August 2009)). There are two main differences between the present method and the ASM approach. The present method does not use a landmark appearance model for boundary searching, because the organ boundary can be determined from the previous segmentation step. Also, this method uses a TPS-based deformable registration after the SSM fitting, because combining SSM with deformable registration could achieve better accuracy than using each alone. The effect of combining SSM with deformable registration will be evaluated and discussed in sections III and IV.

3) Estimation of Low Contrast Organs:

After $\hat{b}^H$ was obtained, the conditional distribution $P(b^L | \hat{b}^H)$ can be calculated using the conditional Gaussian model (equations (16)). Where $\overline{b}^{L|H}$ is the mean value of $P(b^L | \hat{b}^H)$, the estimation of low-contrast organs can be calculated as $$\overline{M}_{Reg}^L = TPS_{final}(\widehat{SIM}(\overline{m}^L + V_L \overline{b}^{L|H})) \quad (18)$$

where $\overline{M}_{Reg}^L$ is the mean shape of the low-contrast organs.

4) Generation of Organ Probability Maps:

$P(b^L | \hat{b}^H)$ gave the conditional distribution of low-contrast organs under the condition of high-contrast organs. Based on $P(b^L | \hat{b}^H)$, an arbitrary number of samples of $b^L$ can be randomly generated. Probability maps of organ distribution can be created based on the random samples. Those probability maps are useful for probability-based image segmentation and quantification.

In practice, $N_s = 100$ samples of $b^L$ were generated. Where $b_i^L$ is the $i^{th}$ sample of $b^L$, $b_i^L$ was converted to organ meshes using $$(M_{Reg}^L)_i = TPS_{final}(\widehat{SIM}(\overline{m}^L + V^L b_i^L)), \quad (19)$$

where $(M_{Reg}^L)_i$ was the mesh union of the low-contrast organs (i.e. the heart, the liver, the spleen and the kidneys). Where $(M_{Reg}^{heart})_i$ is the mesh of heart in $(M_{Reg}^L)_i$, $\{(M_{Reg}^{heart})_i | i=1, 2, \ldots, N_s\}$ is the set of all heart samples. For each sample i, $(M_{Reg}^{heart})_i$ was converted into a binary volume $(BV_{Reg}^{heart})_i$ where the voxels inside the heart mesh were set to value 1, and the outside were set to 0, $(BV_{Reg}^{heart})_i$ had the same matrix size as the CT image. Finally, the probability map of the heart was computed as the average of all $(BV_{Reg}^{heart})_i$s, $$PM^{heart} = \frac{1}{N_s} \sum_{i=1}^{N_s} (BV_{Reg}^{heart})_i \quad (20)$$

where the voxel values of $PM^{heart}$ represented the probabilities of the heart's existence at the locations of these voxels. Similarly, $PM^{liver}$, $PM^{spleen}$, $PM^{L\ kidney}$ and $PM^{R\ kidney}$ were computed.

Probability maps of the high-contrast organs were generated in a similar manner. Where $M_{Reg}^{lungs}$ is the mesh of lungs from $M_{Reg}^H$ (equation (17)), $PM^{lungs}$ was created by filling the voxels inside $M_{Reg}^{lungs}$ with uniform probability. $PM^{skeleton}$ was created in the same way. Unlike the probability maps of low-contrast organs, the probability maps of high-contrast organs were uniform throughout the organ region, because they were registered with the segmentation results, rather than estimated using the conditional Gaussian model.

FIG. 14 step (g) shows the organ probability maps overlaid with the original CT image and FIG. 14 step (h) shows the volume rendering of the organ probability maps.

C. Evaluation of Results

1) Experimental Setup

The statistical atlas-based registration was validated based on both non-contrast micro-CT images and contrast-enhanced micro-CT images. The purpose of this process is to develop a method for non-contrast micro-CT images. However, non-contrast images do not offer good enough soft-tissue contrast for all the target organs. To evaluate the registration accuracy of all the target organs, the strategy described by Baiker (M. Baiker, J. Milles, J. Dijkstra, T. D. Henning, A. W. Weber, I. Que, E. L. Kaijzel, C. W. Lowik, J. H. Reiber, and B. P. Lelieveldt, "Atlas-Based Whole-Body Segmentation Of Mice From Low-Contrast Micro-CT Data," *Med. Image Anal.*, vol. 14, pp. 723-737, (2010)) was used. High-contrast organs (the skin, skeleton and lungs) were evaluated using the non-contrast images, while low-contrast organs (the heart, liver, spleen and kidneys) were evaluated with the assistance of contrast agents, so that the reference standards of the low-contrast organ regions can be defined.

The contrast-enhanced images were selected from the set of images used for atlas construction. A "leave-one-out" test was performed to evaluate the registration accuracy, i.e. each time one of the 45 images was used as a test image and the atlas was constructed from the remaining 44 images. In other words, the test images were not included in the atlases used for comparison.

The method was applied to both non-contrast and contrast-enhanced images. Automatic registration was achieved for all the 23 non-contrast images. However, in 14 of the 45 contrast-enhanced images, the high-contrast organ segmentation step yielded incorrect bone segmentation and manual correction was necessary. This is because the segmentation method was mainly designed for non-contrast images. For contrast-enhanced images, the high-intensity in the liver or spleen may interfere with bone segmentation. After this manual correction, the subsequent registration for the contrast-enhanced images was automatically completed.

The segmentation and registration algorithms were programmed with IDL 7.1 (ITT Visual Information Solutions, Boulder, Colo., USA) and were executed on a PC with a 3.05 GHz CPU and 5.99 GB RAM. The time requirements were ~16 sec for automatic high-contrast organ segmentation (for image size 256×256×496), and ~5 min for atlas registration. Most of the registration time was required for the generation of the probability maps (~4 min 15 sec), the time being directly related to the number of random instances and the volume size of the probability map. 100 random instances and an image size of 256×256×49 were used. Nevertheless, the necessity of probability map generation is optional and depends on user requirements. If the generation of probability maps is eliminated the registration time can be less than 1 min.

2) Visual Assessment of Registration Results

FIG. 15 shows the results of organ probability maps overlaid on non-contrast micro-CT images. Coronal and sagittal slices of different subjects are presented. The probability maps are sown in gray scale, with the brighter portion representing the probability value (brighter portions represent higher probability). FIG. 16 compares the mean shapes of registration results ($M_{Reg}^{H}$ and $\overline{M}_{Reg}^{L}$ in equation (17) and (18)) with the manual segmentation results based on contrast-enhanced images. For every pair of comparison, 'S' stands for manual segmentation result, and 'R' stands for registration result.

3) Registration Accuracy

As described above, for high-contrast organs (skin, skeleton and lungs), the accuracy of atlas registration was evaluated based on 23 non-contrast images, and for low-contrast organs (heart, liver, spleen and kidneys), the accuracy was evaluated based on 45 contrast-enhanced images, via the leave-one-out test. Registration accuracy was measured by comparing the mean shapes of registration results ($M_{Reg}^{H}$ and $\overline{M}_{Reg}^{L}$ in equation (17) and (18)) with the manual segmentation results. Three different metrics, Dice coefficient, recovery coefficient of organ volume ($RC_{vlm}$) and mean surface distance ($D_{surf}$), were used for accuracy assessment:

$$\text{Dice} = 2\frac{|R_R \cap R_S|}{|R_R| + |R_S|}, \quad (21)$$

$$RC_{vlm} = \frac{|R_R|}{|R_S|}, \quad (22)$$

$$D_{surf} = \text{mean}_i \left( \min_j (v_R^i - v_S^j) \right), \quad (23)$$

where $R_R$ and $R_S$ represent the organ regions of registration and segmentation, respectively; |•| denotes the number of voxels, ∩ indicates overlapping between two regions; $v_R$ and $v_S$ represent the surface vertices of the registered region and segmented region, respectively; and i and j denote the vertex index of the two meshes, respectively. The Dice coefficient reflects the estimation accuracy of shape, size and position, $RC_{vlm}$ reflects the estimation accuracy of organ volume, and $D_{surf}$ reflects the average distances between two organ surfaces.

For comparison, single-atlas-based registration was also applied to the test images. Two publicly available mouse atlases, the MOBY phantom and DIGIMOUSE atlas, were used for the comparison. Trunk regions of the two atlases were extracted in the same way as the statistical atlas. The registration on a single atlas was performed as follows: the high-contrast organs were first registered using the RPM method, and then the low-contrast organs were mapped using the transformation obtained from the RPM method. The accuracy of the single atlas registration was also measured by the above three metrics.

FIGS. 17A, 17B and 17C demonstrate the comparison of registration accuracy of major organs between the statistical-atlas-based registration and the two single-atlas-based registrations. Both mean value and standard deviation are plotted. For the Dice coefficient and $RC_{vlm}$, a mean value closer to 1 means better accuracy. For surface distance, mean value closer to 0 mm means better accuracy. It is clear that the statistical-atlas-based registration performs better than the two single-atlas-based registrations. The Dice coefficient and $RC_{vlm}$ for skin and skeleton were not calculated because the skin and skeleton of the atlas are opened meshes which are cut from the whole-body mesh. Opened surfaces cannot be filled into solid volumes for calculating volumetric metrics (Dice and $RC_{vlm}$). Moreover, in the atlas, the skin and skeleton only cover the trunk range, while in the target image, the skin and skeleton cover the whole body range. Therefore it is not appropriate to compute Dice and $RC_{vlm}$ based on different anatomical ranges.

4) Influence of the Number of Training Subjects

Since the statistical atlas is constructed based on multiple subjects, the number of subjects evaluated can be expected to influence the accuracy of registration. A "leave-many-out" test of atlas registration was conducted to quantify this influence. Different numbers of subjects (5, 15, 25, 35 and 44) were used for the atlas construction. For 5, 15, 25 and 35 subjects, the subjects were randomly selected from the total of 45 and the resulting atlas was registered to all the remaining number of subjects (40, 30, 20 and 10). This experiment was repeated five times to reduce the possible bias of random selection. For the case of 44 subjects, the test was the same as "the leave-one-out" test. The means and standard deviations of the Dice coefficient for each number of subjects were obtained and are plotted in FIG. 18. In order to give a clear demonstration, the standard deviations were plotted in different directions for different organs. It can be seen that with increasing subject size, the mean Dice coefficients increase, and the standard deviations generally decrease.

FIG. 18. shows the influence of the number of subjects on registration accuracy. The numbers on the abscissa axis represents the number of subjects used to construct the atlas. Dice coefficient results of different organs are plotted for different numbers of subjects.

5) Comparing Statistical Atlas Registration with TPS-Based Deformable Registration The statistical atlas fitting was combined with TPS-based deformation (see equation (17)). To show the effect of this combination, the accuracies of using each method alone was compared with the accuracies of combing them together. FIG. 19 shows the comparison results in terms of Dice coefficients with both mean values and standard deviations shown. "Statistical Atlas+TPS" represents the combined method. "Statistical Atlas Only" represents performing statistical atlas fitting without TPS-based registration (i.e. ignoring $TPS_{final}$ in equations (17), (18) and (19)). "TPS of Mean Atlas" represents the use of the mean shapes of $SSM^H$ and $SSM^L$ as a single atlas, and registering it with TPS-based deformable registration in the same manner as was done with the MOBY and DIGIMOUSE atlases. "TPS of Single Atlas" means using each of the 45 training subjects as a single atlas, registering them with TPS-based deformable registration, and computing the means and standard deviations of the Dice coefficients for all the 45 single atlases. For all four methods, the same test images were used. "Leave-one-out" tests were performed to avoid including the test images in the atlases.

D. Discussion

1). Atlas Registration

From FIG. 15 it can be seen that the probability maps of low-contrast organs have fuzzy edges and bright centers. This means there is higher probability of the organs' presence in the central regions than in the edge regions. In the probability map of the liver, the cranial part is better defined than the caudal part, because the cranial part is closer to the lungs, which are known as a deterministic condition. Similarly, the probability map of the heart is better defined than other low-contrast organs, because the heart has good correlation with the location of the lungs. The spleen and the left kidney are two of the least well determined organs, since their positions are influenced by the varying size of the flexible stomach. The food content in the stomach influences its size, and consequently influences the positions of the spleen and left kidney. The same phenomenon is also observed from the quantitative results (FIGS. 17A-17C), where the spleen and left kidney always have the poorest accuracy.

As shown by FIG. 17A, the two single subject atlases, MOBY and DIGIMOUSE, have similar levels of Dice coefficients. They outperform each other on different organs, but neither of the two prevails on all organs. The statistical atlas presented here yields larger Dice coefficients than both single atlases which means the statistical atlas described herein provides a superior simulation image. Although a non-rigid deformation (the RPM method) is used for both the statistical atlas and the single atlas registrations, the statistical atlas outperforms the single atlases because it provides a better estimation of the mouse anatomy before the final non-rigid deformation, in the same manner as generating an individual-specific single atlas matches the subject better than any existing single atlas. Observing the results, it is significant that the statistical atlas-based registration obtains Dice coefficients >0.7 for the lungs, heart, liver and kidneys. The statistical atlas also produces small standard deviations for the lungs, heart and liver, but not for the spleen and kidneys. The liver has smaller standard deviation because it is bigger in size and more stable in location. The spleen has the smallest mean Dice coefficient and the biggest standard deviation, because it suffers from both unstable position (affected by the flexible stomach) and problematic shape (banana-like long shape), which makes it very sensitive to small variances of position and direction. The kidneys also have suboptimal standard deviations, because their positions are unstable. It should be noted that the right kidney has larger Dice coefficient and smaller standard deviation than the left kidney because the position of the right kidney is less flexible than the left kidney. The position of the right kidney is mainly affected by the liver, which is big and stable. In contrast, the position of the left kidney is mainly affected by the stomach, which is flexible in size and position.

From FIGS. 17B, 17C and, the results of $RC_{vlm}$ and $D_{surf}$ reveal similar phenomena as the Dice coefficients. The $RC_{vlm}$ of the statistical atlas is close to 1 for almost all organs. This means that the statistical atlas is good at estimating organ volume. For the spleen, the statistical atlas tends to overestimate the spleen volume. The spleen $RC_{vlm}$ of the MOBY atlas is even closer to 1 than the statistical atlas, but the MOBY atlas based registration tends to underestimate the spleen volume. In terms of surface distances, the statistical atlas has smaller distances for all organs than the single atlases. The surface distances of the high-contrast organs are significantly smaller than the low contrast organs, because the high-contrast organs are directly registered to the CT segmentation results. For the statistical atlas, the surface distances of the high-contrast organs are 0.26±0.02 mm for the skin, 0.26±0.05 mm for the skeleton and 0.18±0.01 mm for the lungs. The achievement of this accuracy is attributed to the combination of statistical atlas with the RPM registration method.

FIG. 18 demonstrates the influence of the number of subjects on the Dice coefficient. It is clear that the Dice coefficient of every organ increases when more subjects are used. This phenomenon again confirms the advantage of using more subjects. It can also be observed that the improvement for low-contrast organs is faster than for high-contrast organs. This is because for high-contrast organs, the TPS-based registration (equation (17)) was used to capture more anatomical variations than the SSM captures, while for low contrast organs, no TPS-based registration can be directly applied. Therefore, there was more reliance on the improvement of SSM. From FIG. 18, we can also see that the Dice coefficients for all organs tend to show a lesser increase as the number of subjects becomes larger, implying there might be an upper value of Dice coefficient for each organ. The possible existence of this upper value results in a limitation of the statistical-atlas-based approach and all possible inter-subject anatomical variations may not be included in this approach.

FIG. 19 reveals that combining the statistical atlas with deformable registration yields better accuracy than using each alone. The statistical atlas and deformable registration complement each other to achieve improved accuracy. By fitting the statistical atlas to the subject image, an individualized atlas is obtained and is then used as a starting point of the deformable registration. On the other hand, the deformable registration serves as a compensation for the over-constrained SSM, since the number of subjects is limited compared to the great inter-subject anatomical variations. FIG. 19 also demonstrates that "Statistical Atlas Only" and "TPS of Mean Atlas" have comparable accuracies with each other for low contrast organs, and both of them are more accurate than "TPS of Single Atlas". However, for the lungs, "TPS of Mean Atlas" and "TPS of Single Atlas" are better than the "Statistical Atlas Only", because the lungs are directly registered by the TPS-based method. It thus can be concluded from these observations that TPS-based registration performs well for high-contrast organs because the landmark points of the TPS deformation can be directly obtained from the segmentation of these organs. However, for low contrast organs, the statistical atlas is essential since it uses a conditional Gaussian model to derive subject-specific estimation. Also, using the mean shape of the statistical atlas as a single atlas is more accurate than using an individual subject as a single atlas because the mean shape as a representation of the whole subject set is less prone to the influence of the outlier subjects.

2) Atlas Construction

An issue apparent from FIG. 18 is how many subjects are needed to approach the upper bound of registration accuracy. While 45 subjects is a fairly large number of subjects, the DICE data shows there is still room for improvement with more subjects, as 45 was not enough to model the numerous anatomical variations of a mice population. To achieve better accuracy, the number of samples can be increased and/or the target population variations can be decreased by building and registering the atlas based on subgroups of the population according to different ages, strains, sexes, etc. The synthetic variation methods for statistical shape model construction (J. Koikkalainen, T. Tolli, K. Lauerma, K. Antila, E. Mattila, M. Lilja, and J. Lotjonen, "Methods Of Artificial Enlargement Of The Training Set For Statistical Shape Models" *IEEE Trans. Med. Imag.*, vol. 27, pp. 1643-1654, (November 2008)) incorporated herein in its entirety by reference can also be used to artificially enlarge the variations of limited sets of subjects.

The statistical atlas is constructed based on the segmentation of Fenestra™ LC-enhanced CT images. Most trunk organs that are important for bio-distribution studies are included in the atlas. However, there are a few major trunk organs, such as the bladder and the gastrointestinal (GI) track, not included due to technical difficulties. The difficulties of including the bladder and the GI track are illustrated in FIG. 20. In FIG. 20 the subject is shown at similar coronal positions and at different time points after the injection of contrast agent. The arrows point to the bladder, and the dashed circles roughly delineate the GI regions. It is noticeable that the sizes and positions of the bladder is different when observed at different times due to the influence of urine accumulation. It can be observed that the GI track has fuzzy boundaries in all images, making it difficult to accurately define. Also, since the bladder has significant intra-subject variation, it is very difficult to model its inter-subject statistics. Therefore, the atlas registration strategy appears to be unsuitable to estimate the bladder. Instead it would be easier to extract the bladder via segmentation strategies since the bladder normally presents good boundary contrast. In regard to the GI track, it is hard to clearly define the detailed boundaries from Fenestra™ enhanced images. To overcome this limitation, as well as to define other smaller organs like the gallbladder and pancreas, it appears to be necessary to use multiple CT contrast agents, intraperitonealy administered, or micro-MR images. Another limitation of the current process is that the statistical atlas is constructed using healthy subjects. It is difficult to include unhealthy subjects because different diseases may affect the anatomy in unpredictable ways. However, many pre-clinical studies are conducted based on disease models.

2). Statistical Shape Model and Conditional Gaussian Model

The statistical shape models were constructed for groups of multiple organs. That is, instead of modeling each organ individually, a group of organs is modeled as a single object. The advantage of doing this is that the relative movements between adjacent organs can be inherently built into the model. As a result, the chances of organ overlap are much reduced. However, group-wise modeling tends to over-constrain the model, making it difficult to capture delicate shape variations of single organs. Multi-object statistical shape models can be used to model both inter-organ movements and single organ variations.

The conditional Gaussian model was used in the estimation of low-contrast organs from high-contrast organs. Nevertheless, the value of the conditional Gaussian model can reach beyond this specific application. For example, for those applications that use the mouse body surface to estimate internal organs, the conditional Gaussian model is a good choice for capturing the correlation between internal organs and body surface. Furthermore, it can also be used in clinical image analysis, for the estimation of unknown organs based on the already segmented organs.

4) Comparison with Existing Methods

Several single-subject atlas registration methods have been demonstrated by others. Most existing methods are used for whole-body registration. In contrast, the present method focuses on the trunk region because only this region is stable enough for inter-subject statistical modeling when imaged in the imaging chamber (see FIGS. 23 and 24) utilized. Otherwise if the head, the limbs and the tail are built into the model, they may introduce false statistical correlations caused by posture changing. By focusing on the trunk region, the method resulted in better accuracy than single atlas-based registrations. Therefore, the statistical atlas described herein is suitable for the trunk region, while a single-subject atlas can be used for whole-body registration. In fact, a single-subject skeleton atlas was used for defining the trunk region based on spine and skull alignment, and this strategy can also be used for brain estimation. However, this strategy is not accurate enough for aligning the limbs, especially for the front limbs which are too close to the thoracic bones. It is further contemplated that the trunk atlas can be combined with articulated skeleton atlas or piecewise skeleton registration approach to offer wider usability and better accuracy for mouse micro-CT image registration.

A probabilistic atlas (PA) was generated for the abdominal organs. Previously, PA-based segmentation of human abdominal organs from clinical CT images has become a popular topic. The method set forth herein has a similar application purpose as the existing PA-based methods, namely obtaining probability maps of abdominal organs, but also provides advances in methodology. For the generation of the PA, existing methods register the subjects into a common space either by aligning the target organs themselves or by establishing an external normalization space (such as the abdominal cavity or TPS-based control points), and then estimate the PA by computing the proportional fractions of the aligned binary organs. In the method described herein, the PA is estimated by sampling the analytical distribution of $SSM^L$ rather than by counting from aligned subjects. In this way, the PA is related to the statistical shape model (SSM). The relationship of SSM and PA has not been extensively studied in prior evaluations of the human abdominal CT. Combined SSM and PA for the segmentation of human abdominal organs has been evaluated in the past, but SSM and PA are constructed and applied separately. Pancreas PA have been correlated with the SSM of pancreas centerline, but each instance the SSM had to be endowed with a different PA, making the optimization of individualized PA computationally expensive; hence, only a limited number of pre-sampled SSM instances were used for the optimization. As set forth in the present method, since the conditional distribution of $SSM^L$ is already individualized for the specific subject, it is straight-forward to generate an individualized PA from $SSM^L$. Moreover, for localizing the PA into the individual subject, existing methods normally use the same normalization space of PA construction to map the PA into individual images, and some of these methods also utilize image intensity information for organ pose estimation or atlas registration. In the present method, the PA of low contrast organs is inherently localized according to the analytical anatomical correlation (conditional Gaussian model) with surrounding high contrast organs. The high contrast organs provide both shape condition ($b^H$ in equation 19) and external spatial constraint ($TPS_{final}$ and SIM in equation 19) for the low contrast organs. Such a strategy is useful not only for CT images, but also for other modalities where high contrast organs can help with the estimation of nearby low contrast organs, such as PET images, etc. Finally, in contrast to existing human-oriented references, the PA obtained by the method described herein is not used for segmentation, due to the imperfect soft-tissue contrast of in vivo micro-CT images. Nevertheless, the PA generated by the present method can be useful for segmenting other modalities that are co-registered with the micro-CT images, such as micro-PET, micro-SPECT, etc, One basic assumption of the conditional Gaussian model is that both $b^H$ and $b^L$ follow multivariate Gaussian distributions. In order to verify this assumption, the distributions of the first five principal components of $b^H$ and $b^L$ in scatter plot matrices were evaluated. FIGS. 21A and 21B show the scatter plots of $b^H$ and $b^L$ based on 45 subjects, respectively. The joint distribution of two principal components is plotted in the non-diagonal blocks of the matrices. In the diagonal blocks, a histogram of each principal component is plotted. While the number of subjects is limited, the joint distributions and the histograms roughly follow 2D and 1D Gaussian distributions, respectively. The plots also reveal that the number of subjects is still not enough to support an obvious Gaussian distribution. Therefore, more subject data is needed to improve the quality of the model. FIG. 21B shows the distributions of the first five principal components of $b^L$, plotted in the same way as FIG. 21A.

Another assumption of the conditional Gaussian model is that there should be statistical correlations between the shapes of different organs. In order to verify this assumption, the covariance matrix of different organs was plotted: Where v is the 1D vector that lines-up the vertex coordinates of all organs, $$v = \{x^{skin}, x^{skeleton}, x^{lungs}, x^{heart}, x^{liver}, x^{spleen}, x^{L\,kidney}, x^{R\,kidney}\}, \quad (24)$$

$x^{skin} = \{x_1^{skin}, y_1^{skin}, z_1^{skin}, x_2^{skin}, y_2^{skin}, z_2^{skin}, \ldots, x_N^{skin}, y_N^{skin}, z_N^{skin}\}$, and similarly for other organs.

The correlation matrix of v estimated based on the 45 subjects is plotted in FIG. 22. The pixels of the matrix represent the correlations between every two elements of v. The bright diagonal line throughout the matrix means that every vertex has strong self-correlation. In order to mark the range of different organs, lines can be drawn to divide the matrix into sub-blocks with each sub-block corresponding to the correlation between two organs. The bright portions of the block represents the strength of inter-organ correlations. Some sub-blocks demonstrate good inter-organ correlations, such as the heart vs. the lungs, and the spleen vs. the left kidney. Some organs correlate well with only part of other organs. For example, the kidneys correlate well with part of the skeleton (the abdominal spine), and the right kidney correlates well with part of the liver (the right lobe). It can also be seen that the spleen and the kidneys have very strong self-correlations, meaning these organs have stronger inter-subject translations than the changing of sizes and shapes because, if an organ mainly performs translation without significantly changing its size or shape, the vertices of that organ will always move in similar directions and thus have strong correlations between each other.

In summary, in the method described herein a statistical atlas of the mouse trunk region was constructed, and this atlas was registered to non-contrast mouse micro-CT images to estimate the major organs of trunk region. There is no prior showing that a multi-subject mouse atlas has been proposed for multiple trunk organs. Moreover, differing from probabilistic atlases which are constructed by directly averaging multiple single-subject atlases, the atlas described herein uses statistical models to analytically describe the inter-subject distributions and inter-organ correlations. Subject-specific organ probability maps are generated based on the registration of statistical shape models.

The strategy of combining statistical shape models with conditional Gaussian models can also enrich the methodologies of multi-subject atlas construction. The statistical shape model was used to compensate for inter-subject anatomical variations, and the conditional Gaussian model was used to capture inter-organ shape correlations. The evaluation results showed improvement of registration accuracy compared to single atlas-based registration, and the registration accuracy can be further improved with the increase of the number of subjects. Comparing the statistical-atlas-based registration with TPS-based deformable registration, the statistical atlas demonstrates advantages in improving the accuracy of low-contrast organs.

Sample Collection System

As an aid to establishing the capability to obtain stable and reproducible images of subject animals, a bench-top PET system 100, referred to as the PETbox4, was designed for integrated biological and anatomical preclinical imaging of mouse models. In the present embodiment, as part of the anatomical imaging process using the PETbox4, a mouse atlas registration system (MARS) 110 integrates one or more X-ray projections and one optical images of each subject into the system and registers that information with a predetermined mouse atlas. Alternatively, PET images can also or alternatively be used.

In a preferred embodiment shown in FIGS. 23 and 24, the PETBox4 comprises four x-ray detector panels 114 arranged in a box-like geometry surrounding an inner space (not visible). In this embodiment, each panel 114 is comprised of a 24×50 array with 1.825'1.825×7 mm BGO crystals, coupled to two Hamamatsu H8500 PMTs via a glass light guide. The reconstructed field of view (FOV) is 45×45×94 mm. The signals from the four panels are connected to a 16-channel digitizer board (not shown), with on-board crystal and energy discrimination. The list mode files that are generated are streamed to a PC (not shown) for ML-EM reconstruction based on a parameterized system model of detector responses.

The MARS 110, located in front of a gantry portion of the PETbox4 100, is composed of a top-view x-ray source 108 and a side-view optical camera 112, preferably generating a digital image that can then be manipulated by computer techniques for registration purposes. A miniature x-ray tube (the source 108) is placed 238 mm above the FOV center, and the 98×96 mm x-ray detector 114 is placed 45 mm under the FOV center. The optical camera 112 with a 5 mm focal length lens is placed 185 mm laterally towards the right-side of the FOV center and the mouse which is located in the mouse chamber 116. The mouse chamber 116, which comprises a platform on which the anesthetized mouse is placed and which can have a transparent tubular cover to enclose the mouse, is moveable from an external location to the imaging position within the MARS 110 after the mouse is secured therein. A short duration X-ray projection (40 kVp, 100 μA) and a snap-shot of an optical silhouette are taken for each subject, followed by a 2D/3D registration of a digital mouse atlas to the acquired images, obtaining a 3D estimation of the subject anatomy. The dimensions disclosed are used for typically mouse subjects identified above. One skilled in the art will recognize that the PETbox4 dimensions can be reconfigured for larger or smaller animals as may be appropriate.

System Performance and Experimental Results

For the PETbox4 100, system sensitivity and image spatial resolution were measured with a 20 ns timing window and a 150-650 keV energy window. By placing a drop of $^{18}$F in the FOV center, the peak absolute system sensitivity was measured to be 14%. The image spatial resolution was measured with a 28.3 μCi $^{22}$Na point source (0.3 mm nominal size) placed in the FOV center. Following the NEMA NU4 standards, the reconstructed image spatial resolution was measured for different radial and axial positions in the FOV and ranged from 1.4 to 1.93 mm with an average of 1.46 mm.

Atlas registration accuracy of the MARS 110 was evaluated with two mouse subjects. The subjects were injected with CT contrast agent and were imaged with both the MARS unit 110 and a commercial micro-CT while holding the subject in a fixed position. The CT images were manually segmented as a gold standard and were mapped to the MARS FOV. Dice coefficients for the major organs were computed by comparing the registered atlas with the gold standard (Table 3).

For combined PETbox4/MARS imaging, mice were injected with four different tracers and were imaged at 1 hour post injection. The mice were anesthetized inside an imaging chamber and placed in the M RS FOV for the anatomical acquisition, followed by the PETbox4 acquisition. The registered atlas and the reconstructed PETbox4 images were fused together and are shown in FIGS. 25A, 25B, 25C and 25D. FIG. 25A shows a 10 minute scan of a subject labeled with a 4.6 μCi F-18 gene expression probe. FIG. 25B shows a 30 minute scan of a subject containing 42.4 μCi FDG at scan start time. FIG. 25C shows a 15 minute scan of a subject containing 11.6 μCi Cu-64 labeled antibody fragments. FIG. 25D shows a 20 minute scan, with a subject containing 34.1 μCi NaF In all instances the labeled compound was injected at scan start time.

While reference is made to a mouse atlas and the animal holding portion is referred to as a mouse chamber 116, once skilled in the art will recognize that the utility of the above described device and procedure is not limited to mice and may be applicable to other small laboratory test animals. In such instance an appropriate animal atlas and an appropriate chamber or carrier is used. It should also be recognized that reference to an optical camera or photographic camera or an optical or digital images produced thereby includes all equipment for and all manner of visual, optical, photographic and digital image generation and these terms are used interchangeably.

TABLE 3

ATLAS REGISTRATION ACCURACY FOR MAJOR INTERNAL ORGANS

| | Body | Skeleton | Brain | Lungs | Heart | Liver | Spleen | Kidneys |
|---|---|---|---|---|---|---|---|---|
| Subject 1 | 0.89 | 0.49 | 0.72 | 0.62 | 0.61 | 0.63 | 0.53 | 0.65 |
| Subject 2 | 0.87 | 0.45 | 0.78 | 0.47 | 0.57 | 0.48 | 0.21 | 0.45 |

Accuracy is measured by the Dice coefficient: Dice=2|A∩S|/(|A|+|S|), (Dice∈[0,1]), where A and S are organ regions of the registered atlas and the gold standard, respectively; |•| denotes the number of voxels.

We claim:

1. A method for preparing an image simulating the anatomy of a small subject test animal comprising the use of two or more non-tomographic imaging modalities, said non-tomographic imaging modalities incorporated in a single imaging enclosure including, but not limited to one or more x-ray sources and resultant x-ray projections, photographic cameras and resulting digital or optical images and surface scanners and resultant surface scans, said process comprising:
    placing the subject animal in or on a carrier, the carrier being in the imaging enclosure or inserting the animal and carrier into the image enclosure, such that the location of the test animal on said carrier in the imaging enclosure is a focal point for each of the non-tomographic imaging modalities,
    obtaining a surface scan of the subject test animal, or a combination of one or more of an x-ray projection and a photographic image, or a combination of one or more of an x-ray projection, a photographic or digital image and a surface scan of the subject animal to provide a simulation combination, and
    co-registering the simulation combination with a previously generated digital atlas of the anatomy of the same or similar test animals,
    wherein an iterative process is used to co-register the atlas to the simulation combination obtained by the non-tomographic modalities wherein:
        the non-tomographic modalities are combined to generate a 3D surface mesh based on a mutual information similarity metric and B-Splines,
        the registration results of the non-tomographic modalities are then combined into a 3D deformation which is applied to the atlas to form a deformed atlas, and
        the iteration is repeated until the difference between the atlas and the deformed atlas conforms to a small preset difference between two adjacent iterations.

2. The method of claim 1 wherein said x-ray projection and photographic or digital images are generated from locations at a different angle to the focal point.

3. The method of claim 1 wherein a first x-ray source or photographic camera is positioned at an orthogonal angle to a second x-ray source or photographic camera.

4. The method of claim 1 wherein a combination of the x-ray projections, optical or digital images and scans are generated substantially simultaneously to produce the simulation combination are obtained substantially, simultaneously, sequentially or in overlapping time periods.

5. The method of claim 1 wherein the atlas is co-registered to a top-view X-ray projection, and a side-view image obtained by either or both of an optical camera and a laser surface scammer of the subject test animal.

6. The method of claim 1 wherein the subject test animal is positioned in the imaging enclosure at the focal point and the focal point is the center of a circle perpendicular to a line longitudinally traverse of the test subject to provide a coordinate system with the subject at the center and 0° representing a position on said circle directly above the subject, the combination of non-tomographic imaging modalities comprising one or more of an x-ray source, a camera and a surface scanner, the alternative positions of the non-tomographic imaging modalities comprising
   a. a camera at 0° and a camera at 90°,
   b. a camera at 0° and an x-ray source at 90°,
   c. an x-ray source at 0° and a camera at 90°,
   d. an x-ray source at 0° and an x-ray source at 90°,
   e. an x-ray source at 45° and an x-ray source at 135°,
   f. a scanner only,
   g. an x-ray source at 0° and a scanner,
   h. an x-ray source at 90° and a scanner,
   i. a camera at 90° and a scanner,
   j. an x-ray source at 0°, an x-ray source at 90° a scanner, or
   k. an x-ray source at 0°, a camera at 90° and a scanner.

7. The method of claim 6 wherein an iterative process is used to co-register the atlas to the images obtained by the non-tomographic modalities wherein:
   the non-tomographic modalities are combined to generate a 3D surface mesh based on mutual information and B-Splines,
   the registration results of the non-tomographic modalities are then combined into a 3D deformation which is applied to the atlas to provide a deformed atlas, and
   the iteration is repeated until the difference between the atlas and the deformed atlas conforms to a small preset difference between two adjacent iterations.

8. The method of claim 1 wherein the simulation combination is co-registered to the digital atlas comprising
   a. using 3D deformation techniques, deforming the previously generated digital atlas to produce a deformed digital atlas
   b. preparing a virtual X-ray projection of the deformed atlas, a virtual optical photo silhouette of the deformed atlas, and a virtual image of the body surface of the deformed atlas,
   c. preparing an X-ray projection, an optical photo silhouette from a digital image and a laser scan of the body surface of the target subject,
   d. preparing
      i. a 2D registration of the X-ray projection on the virtual x-ray projection of the deformed atlas, where the resultant 2D deformation is displayed as a deformed 2D grid,
      ii. a 2D registration of the optical photo silhouette on the virtual optical photo silhouette of the deformed atlas, and
      iii. a 3D registration of the laser scan of the body surface on the virtual image of the body surface of the deformed atlas
   e. to produce a co-registered deformed atlas surface, the resulting 3D deformation being displayed as a deformed 3D grid.

9. The method of claim 8 wherein the x-ray projection is a top-view and the digital image is a side-view.

10. The method of claim 8 wherein the procedure described therein is an iterative procedure.

11. The method of claim 1 wherein the digital atlas comprises contrast-enhanced CT images prepared using multiple animal subjects that represent a population similar to the test animals.

12. The method of claim 11 wherein the atlas is generated using multiple animal subjects placed in an image enclosure substantially the same as the image enclosure used to image the test animals.

13. An enclosure for use in generating reproducible images of an animal placed therein and for co-registering the images with a previously generated atlas of internal organs of corresponding animals comprising:
   a. four detector panels arranged in a box-like geometry surrounding a first inner space,
   b. a second inner space enclosing therein two or more non-tomographic image generating devices including but not limited to an x-ray source, an optical camera and a surface scanner, positioned therein to focus on a single internal location and configured for generating images from the two or more image generating devices, wherein the two or more non-tomographic image generating devices are configured to provide a simulation combination,
   c. a subject animal holding chamber movable from a position external of the second inner space to a location within the second inner space, said location within the inner space coinciding with the single internal location, wherein an iterative process is used to co-register the atlas to the simulation combination wherein:
      outputs of the non-tomographic image generating devices are combined to generate a 3D surface mesh based on a mutual information similarity metric and B-Splines
      the registration results of the non-tomographic image generating devices are then combined into a 3D deformation which is applied to the atlas to form a deformed atlas, and
      the iteration is repeated until the difference between the atlas and the deformed atlas conforms to a small preset difference between two adjacent iterations.

14. The enclosure of claim 13 where single internal location in each panel comprises a 24×50 array with 1.825× 1.825×7 mm BGO crystals, said array coupled to PMTs by glass light guides, signals generated by the four panels when the BGO crystals are struck by photons produced by positron emissions being transmitted to a 16-channel digitizer board to produce list mode files that are transmitted to a computer for ML-EM reconstruction based on a parameterized system model of detector responses.

15. The enclosure of claim 13 wherein the x-ray source is positioned approximately 238 mm from the single internal location center, a 98×96 mm x-ray detector is located approximately 45 mm below the single internal location and on a straight line from the x-ray source there through and the optical camera having a 5 mm focal length lens is positioned approximately 185 mm laterally from the single internal location and orthogonal from the x-ray source.

16. The enclosure of claim 13 wherein the atlas is positioned and oriented at the same location as the target subject located at the single internal location.

* * * * *

UNITED STATES PATENT AND TRADEMARK OFFICE
CERTIFICATE OF CORRECTION

PATENT NO. : 9,524,552 B2
APPLICATION NO. : 13/564675
DATED : December 20, 2016
INVENTOR(S) : Hongkai Wang et al.

Page 1 of 1

It is certified that error appears in the above-identified patent and that said Letters Patent is hereby corrected as shown below:

In the Claims

Column 39, Line 27 Claim 6 should read:
"j. an x-ray source at 0°, an x-ray source at 90° and a scanner,"

Signed and Sealed this
Fourteenth Day of March, 2017

Michelle K. Lee
*Director of the United States Patent and Trademark Office*